(12) United States Patent
Ham et al.

(10) Patent No.: US 11,768,196 B2
(45) Date of Patent: Sep. 26, 2023

(54) CURRENT-BASED STIMULATORS FOR ELECTROGENIC CELLS AND RELATED METHODS

(71) Applicant: President and Fellows of Harvard College, Cambridge, MA (US)

(72) Inventors: Donhee Ham, Cambridge, MA (US); Jeffrey T. Abbott, Cambridge, MA (US); Hongkun Park, Cambridge, MA (US); Wenxuan Wu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 685 days.

(21) Appl. No.: 16/625,603

(22) PCT Filed: Jul. 6, 2018

(86) PCT No.: PCT/US2018/040969
§ 371 (c)(1),
(2) Date: Dec. 20, 2019

(87) PCT Pub. No.: WO2019/010343
PCT Pub. Date: Jan. 10, 2019

(65) Prior Publication Data
US 2021/0371846 A1 Dec. 2, 2021

Related U.S. Application Data

(60) Provisional application No. 62/580,126, filed on Nov. 1, 2017, provisional application No. 62/529,683, filed on Jul. 7, 2017.

(51) Int. Cl.
*G01N 33/487* (2006.01)
*C12M 1/42* (2006.01)
(Continued)

(52) U.S. Cl.
CPC ....... *G01N 33/48728* (2013.01); *A61B 5/053* (2013.01); *A61B 5/24* (2021.01);
(Continued)

(58) Field of Classification Search
CPC ........... C12N 13/00; A61B 5/053; A61B 5/24; A61B 2562/0285; A61B 5/7225;
(Continued)

(56) References Cited

U.S. PATENT DOCUMENTS 5,072,194 A 12/1991 Chevallier
5,233,985 A 8/1993 Hudrlik
(Continued)

FOREIGN PATENT DOCUMENTS

DE 19529371 C2 1/1998
EP 1 271 144 A1 1/2003
(Continued)

OTHER PUBLICATIONS

Invitation to Pay Additional Fees for Application No. PCT/US2016/012685 dated Feb. 24, 2016.
(Continued)

*Primary Examiner* — Amy He
(74) *Attorney, Agent, or Firm* — Wolf, Greenfield & Sacks, P.C.

(57) ABSTRACT

Methods and systems for stimulating and monitoring electrogenic cells are described. Some systems for stimulating electrogenic cells are based on the injection of electric currents into the cells via electrodes connected to the cells. Such stimulators may comprise an impedance element having an input terminal and an output terminal coupled to an electrode, and a voltage follower coupled between the input terminal and the output terminal of the impedance element, the voltage follower being configured to maintain a substantially constant voltage between the input terminal and the
(Continued)

output terminal of the impedance element. The impedance element may comprise one or more switched capacitors at least in some embodiments. In some embodiments, the voltage follower may be implemented using a source follower.

18 Claims, 22 Drawing Sheets

(51) Int. Cl.
| | |
|---|---|
| *C12N 13/00* | (2006.01) |
| *G01N 27/00* | (2006.01) |
| *A61B 5/053* | (2021.01) |
| *A61B 5/24* | (2021.01) |
| *A61N 1/18* | (2006.01) |
| *B82Y 15/00* | (2011.01) |

(52) U.S. Cl.
CPC ............... *A61N 1/18* (2013.01); *C12M 35/02* (2013.01); *C12N 13/00* (2013.01); *G01N 27/00* (2013.01); *A61B 2562/0285* (2013.01); *B82Y 15/00* (2013.01)

(58) Field of Classification Search
CPC . C12M 35/02; G01N 27/00; G01N 33/48728; B82Y 15/00; A61N 1/18
See application file for complete search history.

(56) References Cited

U.S. PATENT DOCUMENTS

| | | | |
|---|---|---|---|
| 5,605,612 | A | 2/1997 | Park et al. |
| 7,332,313 | B2 | 2/2008 | Giaever et al. |
| 8,159,300 | B2 | 4/2012 | Masuda et al. |
| 8,227,223 | B2 | 7/2012 | Giaever et al. |
| 9,121,806 | B1 | 9/2015 | Bhansali et al. |
| 9,360,469 | B1 | 6/2016 | Clements et al. |
| 9,700,221 | B2 | 7/2017 | Rajaraman et al. |
| 9,983,198 | B2 | 5/2018 | Chvatal et al. |
| 11,167,131 | B2 | 11/2021 | Isaacs et al. |
| 2002/0010415 | A1 | 1/2002 | Simon et al. |
| 2002/0045318 | A1 | 4/2002 | Chen et al. |
| 2002/0190732 | A1 | 12/2002 | Cheng et al. |
| 2003/0100189 | A1 | 5/2003 | Lee et al. |
| 2004/0100290 | A1 | 5/2004 | Pope et al. |
| 2005/0170510 | A1 | 8/2005 | Huang et al. |
| 2005/0253137 | A1 | 11/2005 | Whang et al. |
| 2005/0282284 | A1 | 12/2005 | Rubinsky et al. |
| 2006/0121446 | A1 | 6/2006 | Abassi et al. |
| 2007/0043301 | A1 | 2/2007 | Martinsen et al. |
| 2007/0072257 | A1 | 3/2007 | Negulescu et al. |
| 2007/0087401 | A1 | 4/2007 | Neilson et al. |
| 2007/0187840 | A1 | 8/2007 | Dell'Acqua-Bellavitis et al. |
| 2007/0264634 | A1 | 11/2007 | Bock et al. |
| 2008/0218939 | A1 | 9/2008 | Marcus et al. |
| 2009/0146735 | A1 | 6/2009 | Jeong |
| 2009/0227066 | A1 | 9/2009 | Joseph et al. |
| 2009/0255801 | A1 | 10/2009 | Hass |
| 2010/0304425 | A1 | 12/2010 | Speller |
| 2011/0210718 | A1 | 9/2011 | Vana et al. |
| 2011/0233512 | A1 | 9/2011 | Yang et al. |
| 2011/0253982 | A1 | 10/2011 | Wang et al. |
| 2012/0094328 | A1 | 4/2012 | Park et al. |
| 2012/0157804 | A1 | 6/2012 | Rogers et al. |
| 2012/0182168 | A1 | 7/2012 | Shibata et al. |
| 2013/0041235 | A1 | 2/2013 | Rogers et al. |
| 2013/0041282 | A1* | 2/2013 | Park .................. A61B 5/0538 600/547 |
| 2013/0072775 | A1 | 3/2013 | Rogers et al. |
| 2013/0123136 | A1 | 5/2013 | Abassi et al. |
| 2013/0260467 | A1 | 10/2013 | Park et al. |
| 2013/0338746 | A1 | 12/2013 | Guvanasen et al. |
| 2014/0001041 | A1 | 1/2014 | Rahman et al. |
| 2014/0057283 | A1 | 2/2014 | Wang et al. |
| 2015/0005680 | A1 | 1/2015 | Lipani |
| 2015/0027885 | A1 | 1/2015 | Rajaraman et al. |
| 2015/0148863 | A1 | 5/2015 | Yun et al. |
| 2015/0376811 | A1 | 12/2015 | Joung et al. |
| 2015/0377856 | A1 | 12/2015 | Dunbar et al. |
| 2016/0047770 | A1 | 2/2016 | Tyler et al. |
| 2016/0096173 | A1 | 4/2016 | Teich et al. |
| 2016/0245790 | A1 | 8/2016 | Kawai et al. |
| 2016/0278713 | A1 | 9/2016 | Shoaran et al. |
| 2017/0058246 | A1 | 3/2017 | Grier, Jr. et al. |
| 2017/0176414 | A1 | 6/2017 | Abdolahad et al. |
| 2018/0163165 | A1 | 6/2018 | Grier, Jr. et al. |
| 2018/0169403 | A1 | 6/2018 | Park et al. |
| 2018/0246079 | A1 | 8/2018 | Wang et al. |
| 2020/0064336 | A1 | 2/2020 | Zafar et al. |
| 2020/0292482 | A1 | 9/2020 | Ham et al. |
| 2021/0187280 | A1 | 6/2021 | Park et al. |
| 2021/0236033 | A1 | 8/2021 | Butera et al. |

FOREIGN PATENT DOCUMENTS

| | | |
|---|---|---|
| JP | 2008-269725 A | 11/2008 |
| WO | WO 2009/137440 A1 | 11/2009 |
| WO | WO 2012/050876 | 4/2012 |
| WO | WO 2012/050881 | 4/2012 |
| WO | WO 2016/112315 | 7/2016 |
| WO | WO 2019/010343 A1 | 1/2019 |
| WO | WO 2019/089495 A1 | 5/2019 |
| WO | WO 2021/257686 A1 | 12/2021 |
| WO | WO 2021/257701 A1 | 12/2021 |
| WO | WO 2021/257705 A1 | 12/2021 |

OTHER PUBLICATIONS

International Search Report and Written Opinion for Application No. PCT/US2016/012685 dated May 3, 2016.
International Preliminary Report on Patentability for PCT/US2016/012685 dated Jul. 20, 2017.
Invitation to Pay Additional Fees for Application No. PCT/US18/58081 dated Jan. 1, 2019.
International Search Report and Written Opinion for Application No. PCT/US18/58081 dated Mar. 22, 2019.
Invitation to Pay Additional Fees for Application No. PCT/US18/40969 dated Aug. 31, 2018.
International Search Report and Written Opinion for Application No. PCT/US18/40969 dated Nov. 2, 2018.
International Preliminary Report on Patentability for Application No. PCT/US18/40969 dated Jan. 16, 2020.
International Preliminary Report on Patentability for Application No. PCT/US2018/058081 dated May 14, 2020.
International Search Report and Written Opinion for Application No. PCT/US2021/037604 dated Sep. 29, 2021.
International Search Report and Written Opinion for Application No. PCT/US2021/037626 dated Sep. 22, 2021.
International Search Report and Written Opinion for Application No. PCT/US2021/037630 dated Sep. 28, 2021.
Abbott et al., Multi-parametric functional imaging of cell cultures and tissues with a CMOS microelectrode array. Lab Chip. Mar. 29, 2022;22(7):1286-1296. doi: 10.1039/d11c00878a.
Crescentini et al., Noise limits of CMOS current interfaces for biosensors: a review. IEEE Trans Biomed Circuits Syst. 2014;8(2):278-292.
Kim et al., An area-efficient low-noise CMOS DNA detection sensor for multichannel nanopore applications. Sensors and Actuators B: Chemical. Jan. 2013;176:1051-1055.
Laborde et al., Real-time imaging of microparticles and living cells with CMOS nanocapacitor arrays. Nat Nanotechnol. Sep. 2015;10(9):791-5. doi: 10.1038/nnano.2015.163. Epub Aug. 3, 2015.

(56) References Cited

OTHER PUBLICATIONS

Park et al., 1024-Pixel CMOS Multimodality Joint Cellular Sensor/Stimulator Array for Real-Time Holistic Cellular Characterization and Cell-Based Drug Screening. IEEE Trans Biomed Circuits Syst. Feb. 2018; 12(1): 80-94. Author manuscript provided. 45 pages.

* cited by examiner

TABLE I
REPRESENTATIVE VALUES OF RESISTORS AND CAPACITORS IN THE CRITICAL SIGNAL PATH OF THE CURRENT STIMULATOR AND ASSOCIATED TIME CONSTANTS

| Parameters | Numerical values |
|---|---|
| Switch on-resistance, $R_{SW}$ | < 10 kΩ (by design) |
| Switched capacitance, $C_{SC}$ | 10 fF or 100 fF (by design) |
| Load capacitance, $C_L$ | 1 pF ~ 100 pF (typical range, dependent upon electrode size and material) [37]. Note that $C_L \gg C_{SC}$. |
| Load resistance, $R_L$ | MΩ ~ GΩ (typical range, dependent upon electrode size, material, and also the output current/voltage). Note that $R_L \gg R_{SW}$. |
| $\tau_1 = R_{SW} C_{SC}$ | < 1 ns |
| $\tau_2 = R_{SW} C_L C_{SC}/(C_L + C_{SC}) \approx R_{SW} C_{SC}$ | < 1 ns |
| $\tau_L \approx R_L C_L$ | > 10 μs and widely varying depending on the size of the electrode, electrode material, and output current/voltage. Note that $\tau_L \gg \tau_1, \tau_2$. |

FIG. 14A

TABLE II
DEMONSTRATED CMOS ELECTRODE ARRAY IN VITRO CURRENT STIMULATION CIRCUITS

| Reference | Technology (μm) | Intended Stimulation Type | Circuit Area (mm²) | Current Source Topology | Output Current Range | Output Voltage Range |
|---|---|---|---|---|---|---|
| This work | 0.18 μm | extracellular/ intracellular | 0.003 | in situ clock frequency to current | 20 pA to 700 nA | 2.4 V |

FIG. 14B

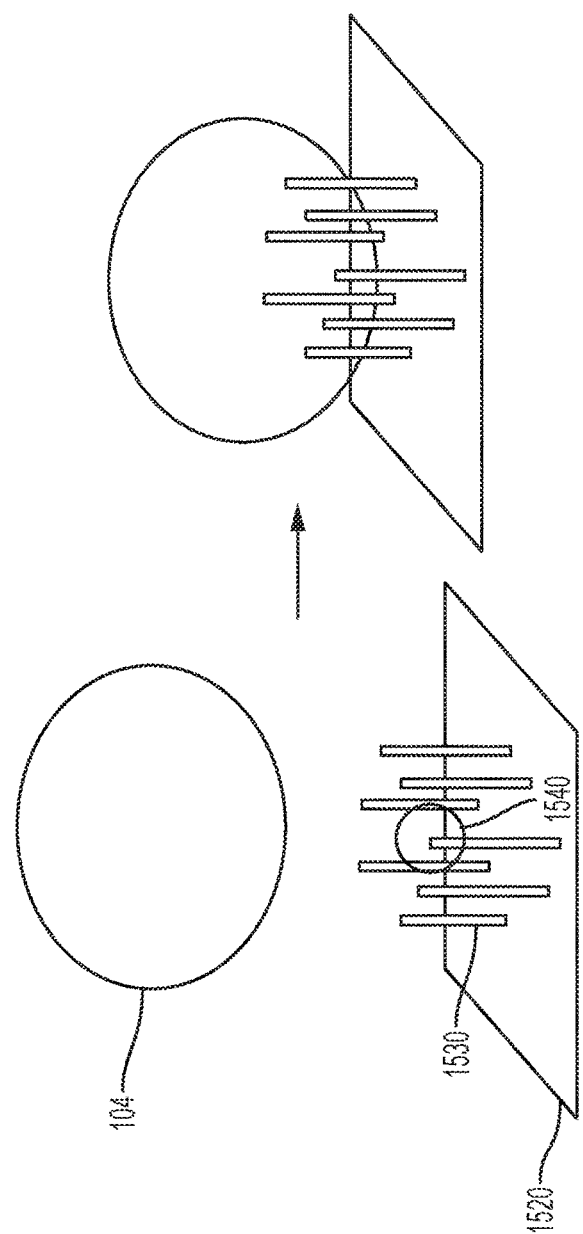

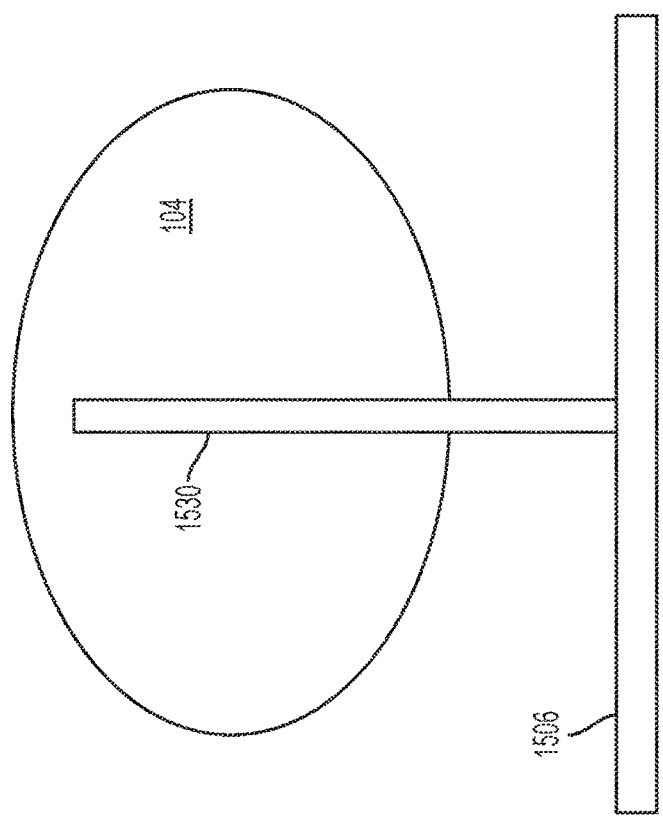

CURRENT-BASED STIMULATORS FOR ELECTROGENIC CELLS AND RELATED METHODS

RELATED APPLICATIONS

The present application is a national stage filing under 35 U.S.C. § 371 of international PCT application PCT/US2018/040969, entitled "CURRENT-BASED STIMULATORS FOR ELECTROGENIC CELLS AND RELATED METHODS," filed Jul. 6, 2018, which is incorporated by reference herein in its entirety, and which claims the benefit under 35 U.S.C. § 119(e) of U.S. Provisional Patent Application Ser. No. 62/529,683 entitled "CURRENT-BASED STIMULATORS FOR ELECTROGENIC CELLS AND RELATED METHODS," filed Jul. 7, 2017, which is incorporated herein by reference in its entirety, and claims the benefit under 35 U.S.C. § 119(e) of U.S. Provisional Patent Application Ser. No. 62/580,126 entitled "ELECTRONIC CIRCUITS FOR ANALYZING ELECTROGENIC CELLS AND RELATED METHODS," filed Nov. 1, 2017, which is incorporated herein by reference in its entirety.

GOVERNMENT SUPPORT

This invention was made with government support under MH105960 awarded by National Institutes of Health (NIH) and under W911NF-15-1-0565 awarded by U.S. Army Research Laboratory (ARL) and under W911NF-15-1-0548 awarded by U.S. Army Research Office (ARO). The government has certain rights in this invention.

BACKGROUND

The present application relates to stimulation and monitoring of electrogenic cells, such as brain cells, heart cells, endocrine cells, and other muscular cells.

BRIEF SUMMARY

According to one aspect of the present application, an apparatus is provided. The apparatus may comprise an electrogenic cell, an electrode electrically in contact with the electrogenic cell, a stimulation circuit coupled to the electrode, the stimulation circuit comprising: an impedance element having an input terminal and an output terminal coupled to the electrode; and a voltage follower coupled between the input terminal and the output terminal of the impedance element, the voltage follower being configured to maintain a substantially constant voltage between the input terminal and the output terminal of the impedance element.

In some embodiments, the impedance element comprises a switched capacitor.

In some embodiments, the apparatus further comprises a control circuit coupled to the switched capacitor, the control circuit having a frequency tuner.

In some embodiments, the electrogenic cell and the electrode form a load having a first capacitance, and wherein the switched capacitor has a second capacitance that is lower than the first capacitance.

In some embodiments, the voltage follower comprises one or more transistors arranged in a source follower configuration.

In some embodiments, the one or more transistors comprise a respective gate terminal coupled to the output terminal of the impedance element and a respective source terminal coupled to the input terminal of the impedance element.

In some embodiments, the apparatus further comprises control circuitry configured to electrically couple the source follower to the input terminal of the impedance element during a first time period and to electrically couple the source follower to the output terminal of the impedance element during a second time period different than the first time period.

In some embodiments, the first time period and the second time period do not overlap in time.

In some embodiments, the stimulation circuit lacks operational amplifiers.

In some embodiments, the electrogenic cell is selected from the group consisting of a brain cell, a heart cell and an endocrine cell.

In some embodiments, the apparatus further comprises an operational amplifier coupled to the voltage follower; and a receiver circuit coupled to the electrode and comprising a high-frequency cutting filter configured to block ripples generated by the stimulation circuit.

According to another aspect of the present application, a method for electrically stimulating an electrogenic cell is provided. The method may comprise generating an output current by: causing an input voltage of an impedance element to follow an output voltage of the impedance element, and coupling the output voltage to an electrode coupled to the electrogenic cell; and driving the electrogenic cell with the output current.

In some embodiments, causing the input voltage of the impedance element to follow the output voltage of the impedance element comprises causing a first terminal of a transistor to follow a second terminal of the transistor.

In some embodiments, causing the input voltage of the impedance element to follow the output voltage of the impedance element comprises causing a source terminal of a transistor to follow a gate terminal of the transistor.

In some embodiments, the method further comprises charging the impedance element during a first time period and discharging the impedance element during the second time period different than the first time period.

In some embodiments, driving the electrogenic cell with the output current is performed in the second time period.

In some embodiments, the first time period and the second time period do not overlap in time.

According to yet another aspect of the present application, a method for monitoring an electrogenic cell is provided. The method may comprise decreasing an input impedance of the electrogenic cell by driving an output current through an electrode placed in contact with the electrogenic cell, and sensing electric signals generated by the electrogenic cell with an amplifying circuit coupled to the electrode.

In some embodiments, driving the output current through the electrode comprises: causing an input voltage of an impedance element to follow an output voltage of the impedance element, and coupling the output voltage to the electrode.

In some embodiments, causing the input voltage of the impedance element to follow the output voltage of the impedance element comprises causing a source terminal of a transistor to follow a gate terminal of the transistor.

In some embodiments, driving the output current through the electrode comprises driving a direct current (DC) for at least one minute.

In some embodiments, the output current is controlled to alternate between two or more values.

According to yet another aspect of the present application a method for manufacturing a current-based electrogenic stimulator is provided. The method may comprise forming an electrode; forming a stimulation circuit coupled to the electrode, wherein forming the stimulation circuit comprises: forming an impedance element having an input terminal and an output terminal coupled to the electrode; and forming a voltage follower coupled between the input terminal and the output terminal of the impedance element.

In some embodiments, the stimulation circuit and the electrode are disposed on a common substrate.

In some embodiments, forming the impedance element comprises forming a switched capacitor.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 14A-14B are tables illustrating representative circuit parameters, according to some non-limiting embodiments.

FIG. 15A is a schematic diagram illustrating an array of nanowires before and after insertion into a cell, according to some non-limiting embodiments.

FIG. 15B is a schematic diagram illustrating a nanowire connected to a metal pad and inserted into a cell, according to some non-limiting embodiments.

DETAILED DESCRIPTION

I. Overview

Figure 1:
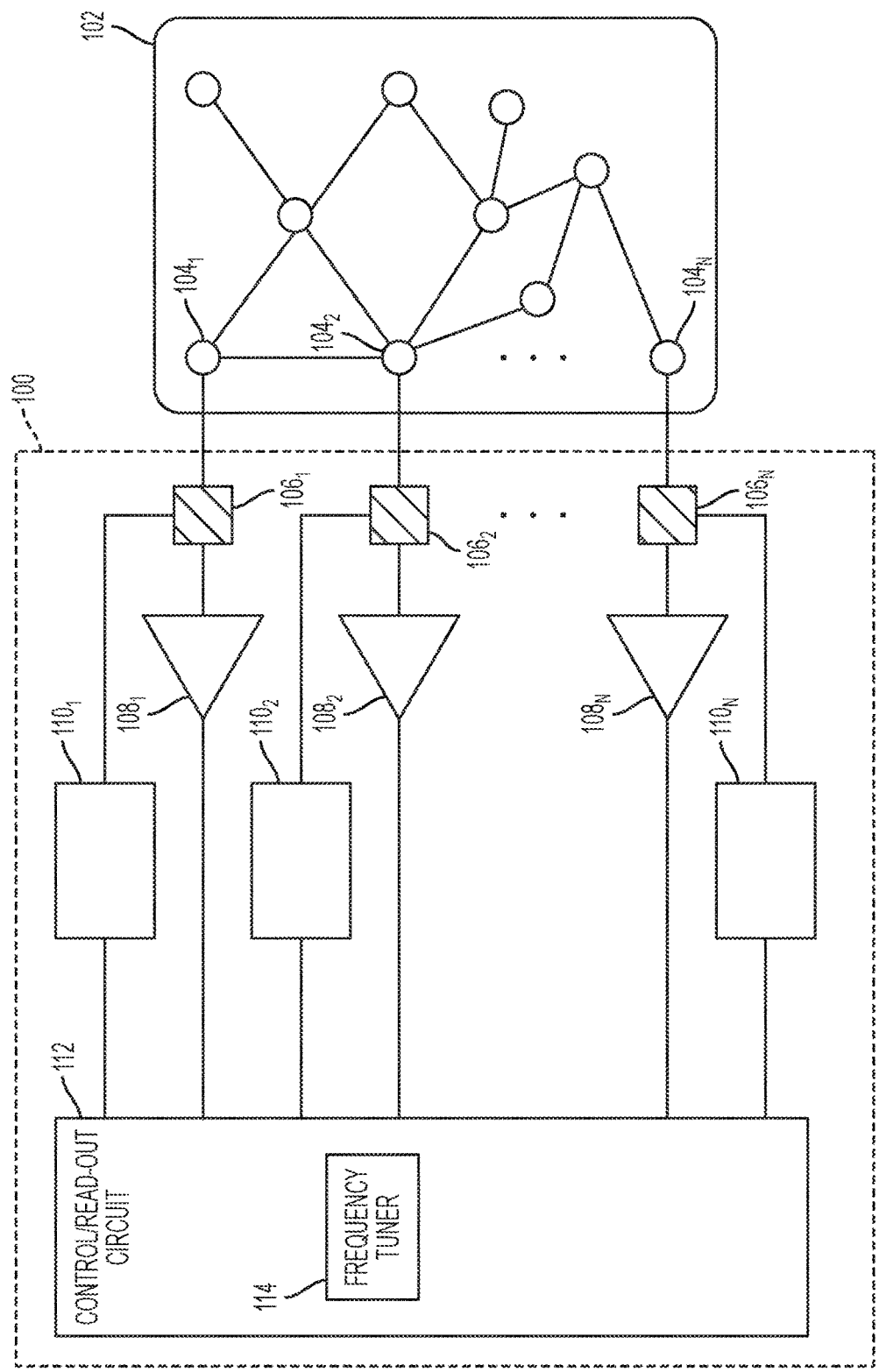
FIG. 1 is schematic diagram illustrating an electrogenic network and a probing system, according to some non-limiting embodiments.

The inventors have recognized and appreciated that stimulation of electrogenic cells may be improved relative to conventional techniques by using current stimulators. Unlike conventional stimulators, these current stimulators may be configured to accurately control the amount of electric charge, and hence of electric current, provided to an electrogenic cell. As a result, delivery of large currents that can seriously harm the integrity of a cell (which often occur in conventional stimulators) may be prevented.

Electrogenic cells are biological cells that are capable of generating and/or responding to electric signals. Electrogenic cells can be arranged in networks, where the cells communicate with other cells of the network via electric signals (referred to herein also as bioelectric events). Examples of electrogenic cells include, but are not limited to, brain cells, heart cells, endocrine cells, and other muscular cells. Action potentials are one example of these electric signals. Action potentials occur in several types of biological cells and can be generated by special types of voltage-gated ion channels embedded in a cell's plasma membrane. These channels may be shut when the membrane potential is near the resting potential of the cell, and may be opened if the membrane increases to a precisely defined threshold voltage.

The inventors have further recognized and appreciated that, in some circumstances, it is desirable to simultaneously stimulate multiple electrogenic cells (e.g., a few thousands, a few millions, or even more) to control and/or characterize the behavior of the overall electrogenic network. As such, large arrays of stimulators may be needed to stimulate each cell individually. However, the size of conventional stimulators limits the number of stimulators that can be integrated on a single circuit, such as a single chip. Some embodiments of the present application are directed to stimulators having small footprints, thus enabling the integration of multiple stimulators onto a single circuit. Such a reduction in the size of the stimulators can be achieved, at least in some embodiments, by employing circuit elements that can be implemented using a small number of transistors or other electric components. Accordingly, in some such embodiments, the stimulator lacks circuits including large number of transistors (such as more than fifty transistors), such as operational amplifiers or other circuits having a voltage gain that is greater than one.

Some embodiments of the present application are directed to stimulators capable of controlling the amount of current provided to an electrogenic cell with a high precisions (e.g., within few nanoamperes (nA), within a few picoamperes (pA) or less). Such precise control of the current may be achieved, at least in some embodiments, by employing an impedance element having an adjustable resistance and a voltage follower. In these embodiments, the amount of current output by the stimulator may be set by setting the value of the impedance element's resistance. The voltage follower may be configured to stabilize the voltage across the terminals of the impedance element, and as a result, the output current. In some such embodiments, the impedance element comprises a switched capacitor, and the resistance of the switched capacitor may be set by varying the frequency of the signal driving the impedance element.

Some embodiments of the present application are directed to systems and methods for monitoring the electric activity of one or more electrogenic cells. Due to the large impedance of electrogenic cells relative to the surrounding environment, obtaining signals from the cells that accurately represent the cell's activity is often challenging. The inventors have recognized and appreciated a method for improving the ability to electrically probe these cells by reducing the impedance of the cells. In some embodiments, a reduction in a cell's impedance may be achieved by generating a potential difference between the electrode used to probe the cell and a node positioned adjacent the cell. This potential difference may be generated, at least in some embodiments, by forcing an electric current to flow through the electrode. Once this potential difference is established, the difference in impedance between the cell and the surrounding environment may be reduced, thus facilitating electric probing of the cell.

II. Electrogenic Stimulators

FIG. 1 is a schematic diagram illustrating an electrogenic network and a probing system. Probing system 100 may be implemented, in some embodiments, using electronic circuits such as CMOS circuits. Electrogenic network 102 comprises a plurality of electrogenic cells $104_1$, $104_2$ ... $104_N$. These cells may be interconnected with one another is any suitable fashion and may communicate with one another via electric signals, such as action potentials. The cells of electrogenic network 102 may be probed using probing system 100 in vitro, in vivo, or in any other suitable way.

These cells may be brain cells, heart cells, endocrine cells, or other types muscular cells. N may be between 1 and 10, between 1 and 100, between 1 and 1000, between 1 and 10000, between 1 and 100000, or greater than 100000.

Probing system 100 may comprise electrodes $106_1$, $106_2$ ... $106_N$, receivers $108_1$, $108_2$ ... $108_N$, stimulators $110_1$, $110_2$ ... $110_N$, and control read-out circuit 112. In some embodiments, these components of probing system 100 are integrated on a single integrated circuit. Of course, multiple integrated circuits may be used, as the application is not limited in this respect.

Electrodes $104_1$, $104_2$ ... $104_N$ may be placed in electrical contact with respective electrogenic cells. For example, the electrogenic cells may be placed in a container with an electrically conductive solution, and the electrodes may be placed in the solution. The electrodes may have areas ranging from 1 nm$^2$ to 1 cm$^2$, though other ranges are also possible.

Stimulators $110_1$, $110_2$ ... $110_N$ may be electrically connected to respective electrodes, and may be configured to stimulate respective electrogenic cells. In some embodiments, the stimulus may be an electric current. Representative implementations for the stimulators are described further below. When stimulated with an electric signal, an electrogenic cell may in response produce electric activity in conjunction with other cells of the network.

As will be described further below, the amount of current provided to a cell may be controlled, at least in some embodiments, by setting the frequency with which a stimulator is driven. As such, the stimulators $110_1$, $110_2$ ... $110_N$ may be coupled to frequency tuner 114, a circuit configured to generate electric signals with a desired frequency. The frequency may be varied in any of numerous ways, including, for example, with a controllable oscillator.

Receivers $108_1$, $108_2$ ... $108_N$ may be configured to monitor the electric activity of the respective cells. For example, the receivers may sense electric signals, such as voltages or currents, which may be representative of the cells' action potentials. In some embodiments, receivers $108_1$, $108_2$ ... $108_N$ comprise signal amplifiers (e.g., voltage amplifiers or transimpedance amplifiers).

Figure 2:
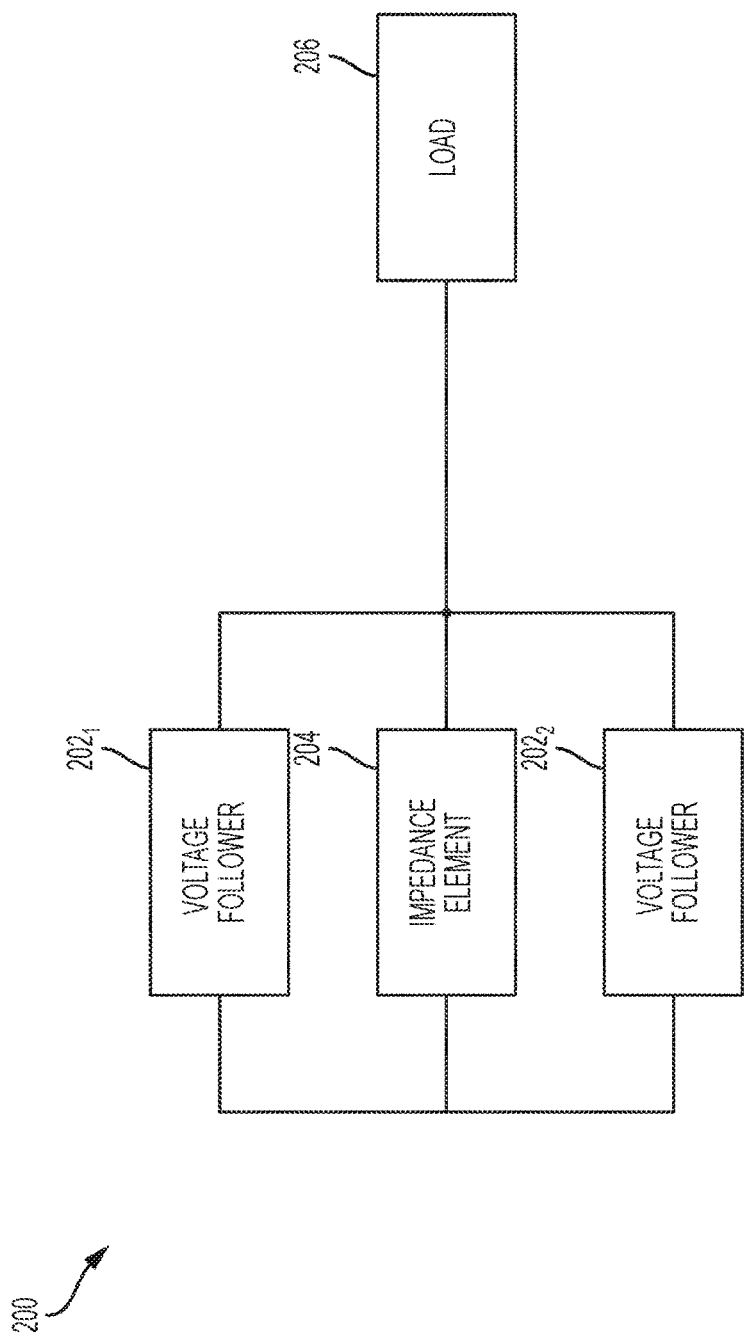
FIG. 2 is a block diagram of a representative electrogenic stimulator, according to some non-limiting embodiments.

In some embodiments, the stimulators may be configured to stimulate the cells by providing them with electric currents, and as such may comprise circuits for sourcing electric currents. A representative system for sourcing electric currents is illustrated in FIG. 2. Stimulator 200 comprises an impedance element 204, a first voltage follower $202_1$ and a second voltage follower $202_2$. While two voltage followers are shown in this example, any suitable number of voltage followers greater than or equal to one may be employed. Stimulator 200 is coupled to load 206, which may reflect the electric characteristics of an electrode 106 and/or a cell 104. Depending on the type of cell and/or electrode, the load 206 may be a resistive load, a capacitive load, or any combination thereof.

Impedance element 204 may have an output terminal coupled to load 206, and an input terminal. Electric currents may be provided to the load via the output terminal. In some embodiments, the voltage follower(s) may be coupled between the output terminal and the input terminal of impedance element 204. Impedance element 204 may be implemented in any of numerous ways, including but not limited to a resistor (or a combination of resistors), a capacitor (or a combination of capacitors), and/or one or more switched capacitors (e.g., one or more capacitors and one or more switches).

In some embodiments, impedance element 204 may be configured to provide the load with a current that is proportional to the difference between the voltage appearing at its input terminal and the voltage appearing at its output terminal. However, such a voltage difference may fluctuate over time, thus leading to a fluctuating current. Such behavior is often undesirable as it diminishes the ability to stimulate different cells uniformly.

Voltage followers $202_1$ and $202_2$ may be arranged to limit fluctuations in the current provided to the load. For example, the voltage followers may be configured to ensure that the voltage appearing at the input terminal of the impedance element follows the voltage appearing at the output terminal of the impedance element. In this way, the difference between the voltages may remain substantially constant over time, thus limiting current fluctuations.

In some embodiments, only one voltage follower may be active at a time. For example, voltage follower $202_k$ may be active during a first time period while voltage follower $202_2$ may be deactivated (for example by opening a switch). The opposite configuration may occur during a second time period. In this manner, no voltage sources are activated in parallel at the same time.

III. Monitoring of Electrogenic Activity

Figure 3A:
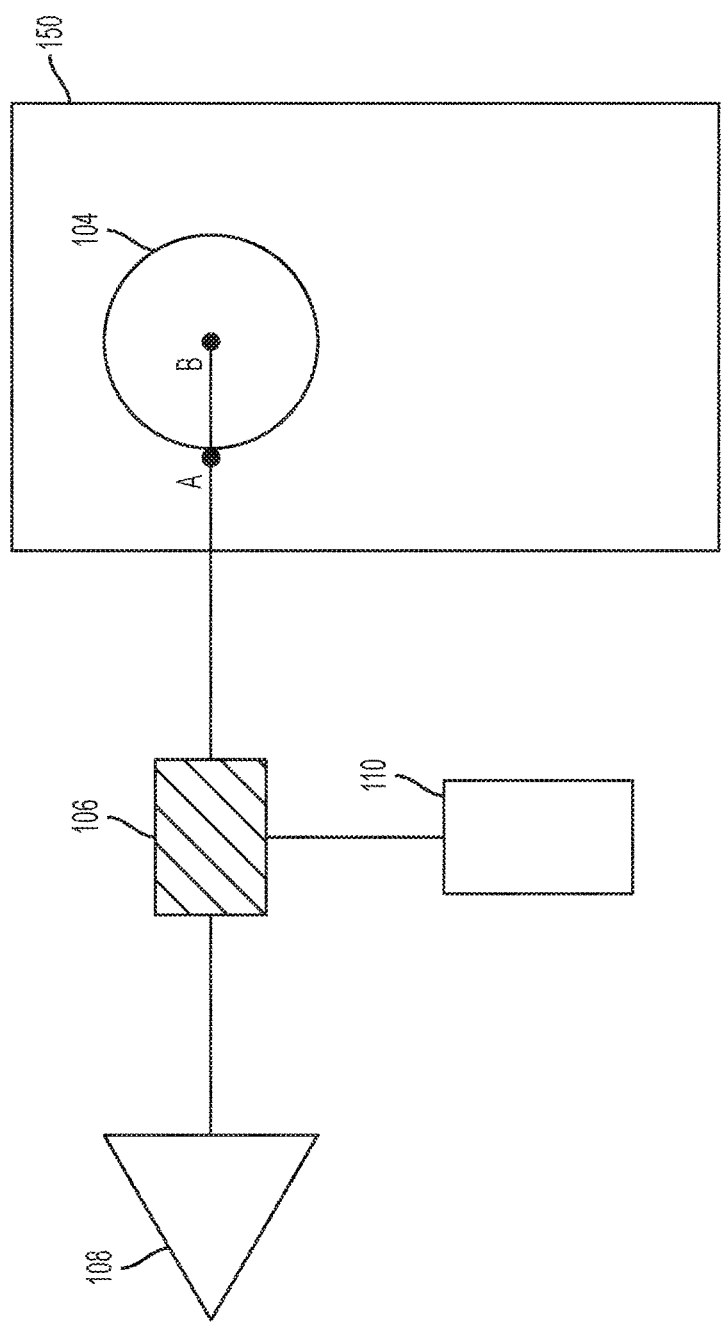
FIG. 3A is a schematic diagram of a representative system for monitoring electrogenic activity, according to some non-limiting embodiments.

As described above, electrogenic cells stimulators may be employed to stimulate cells to produce electrogenic activity. However, stimulators of the types described herein may be used in different settings. One such setting is in the monitoring of electrogenic activity. FIG. 3A illustrates a non-limiting implementation of an electrogenic stimulator used in electrogenic monitoring. As illustrated, electrode 106 is coupled to receiver 108, to stimulator 110 (which may be implemented according to any of the embodiments described above and below), and to cell 104. Cell 104 may be placed in a container 150, which may comprises for example an electrolyte. In the embodiments in which the container includes an electrolyte, the impedance of the electrolyte may be substantially lower than the impedance of the cell 104. As a result, electrically probing of the cell using receiver 108 may be challenging, since the majority of the signal received would solely (or for the most part) depend on the impedance of the electrolyte, rather than the impedance of the cell.

In some embodiments, the impedance of the cell at location "B" (inside the cell), may be decreased by generating a voltage between electrode 106 and a location "A" (outside the cell). This voltage may be generated for example by forcing a current sourced by stimulator 110 to flow through electrode 106. When such a current is flown, the impedance at location A is decreased. As a result, the impedance at location B relative to the surrounding electrolyte is also decreased, thus facilitating the monitoring of the cell's electrogenic activity.

In some embodiments, current may be sourced by the stimulator for the duration of a monitoring session, which may range between one second and several hours.

Figure 3B:
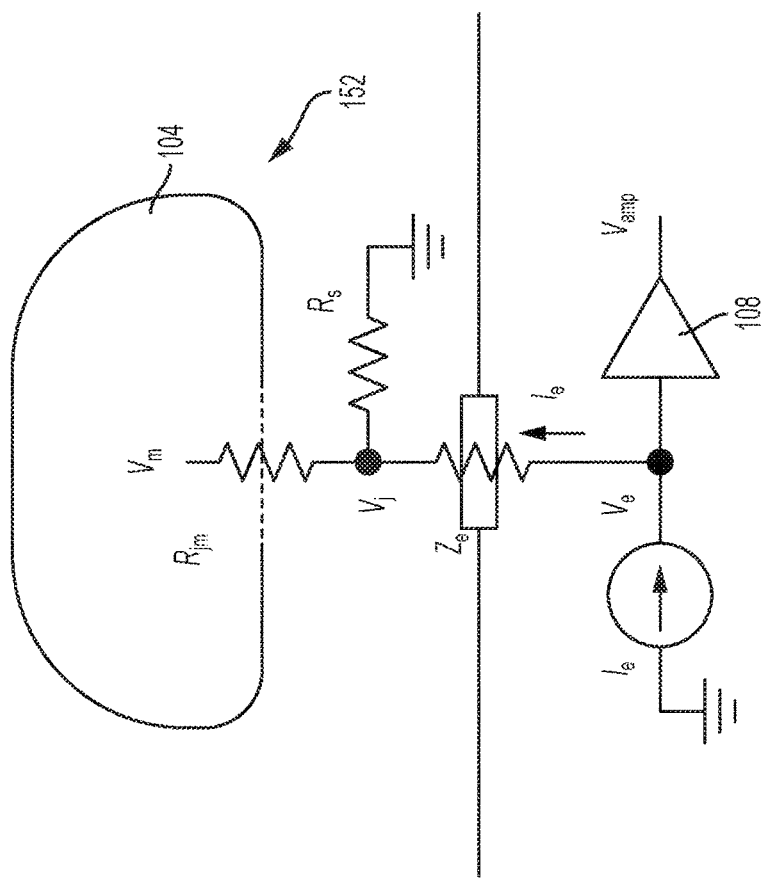
FIG. 3B is a circuit diagram of a representative system for monitoring electrogenic activity, according to some non-limiting embodiments.

FIG. 3B is a circuit diagram illustrating a system for monitoring electrogenic activity, according to some embodiments. As shown, a cell 104 is immersed in an electrolyte 152, which may be contained inside container 150 of FIG. 3A. The cell exhibits an input resistance $R_{jm}$, which may be for example more than 10 GΩ or more than 100 GΩ. Voltage $V_m$ (the quantity to be sensed) may represent for example an action potential.

Electrode 106 is represented in FIG. 3B by its impedance $Z_e$. The electrode is coupled to receiver 108. $R_s$ represents the resistance of the electrolyte, which may be for example between 1MΩ and 100MΩ. Since $R_{jm}$ is, at least in some embodiments, a few orders of magnitude greater than $R_s$, attempts to sense to sense $V_m$ using receiver 108 will result in the sensing of $V_j$, rather than $V_m$. The inventors have appreciated, however, that sensing of $V_m$ may be enabled by injecting (or extracting) a current through the electrode into the electrolyte, which results in a substantial decrease in the value of $R_{jm}$. Accordingly, stimulator 110 includes a current generator $I_e$ configured to drive a current through the electrolyte.

Figure 3C:
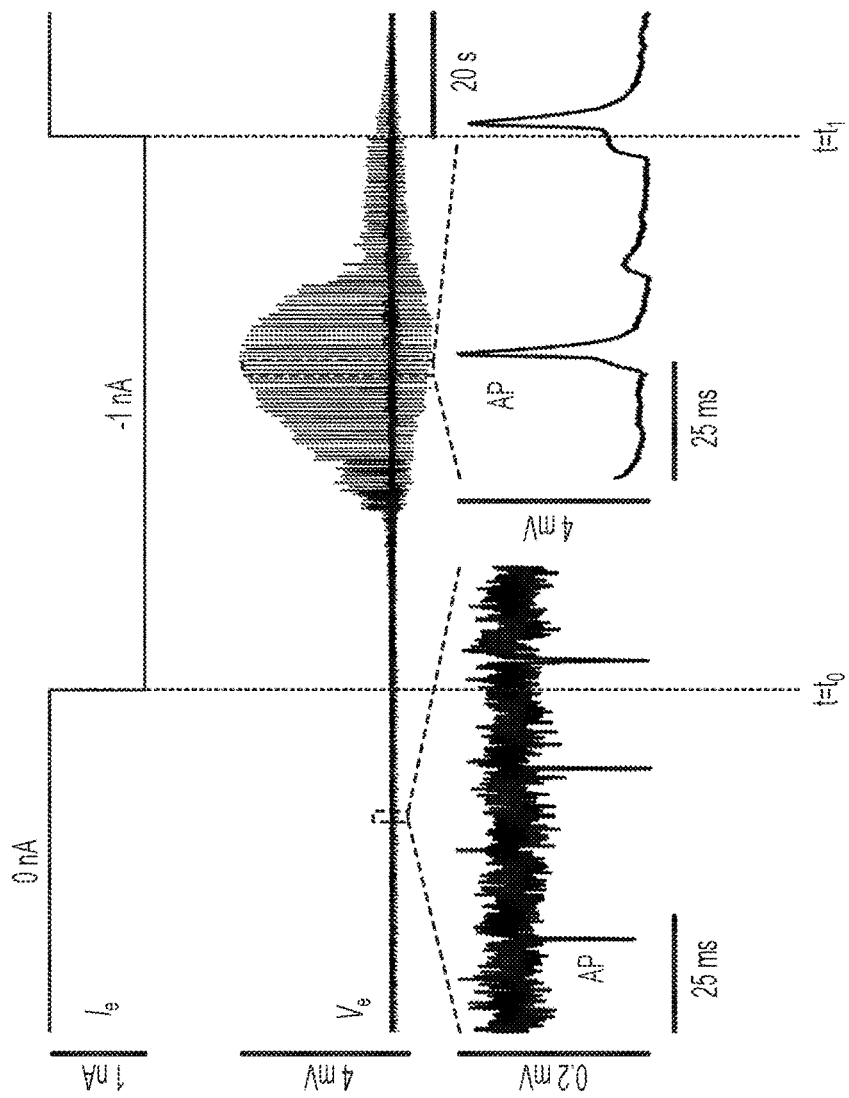
FIG. 3C is a plot illustrating the voltage obtained when a cell is probed using the system of FIG. 3B, according to some non-limiting embodiments.

FIG. 3C is a plot illustrating the response of the system when a current is generated with the current generator of FIG. 3B. Specifically, FIG. 3C illustrates an example of a current $I_e$, and the response of the system in terms of voltage $V_e$, at the electrode 106. Prior to $t=t_0$, no current is generated (0 nA). In this period of time, voltage $V_e$ exhibits an amplitude of the order of 0.2 mV. Voltage peaks of about 0.1 mV in amplitude are observed. Given their low amplitude, these peaks are an attenuated and distorted representation of the intracellular activity (e.g., action potentials).

At $t=t_0$, the current $I_e$ output by the current generator is set to −1 nA (where the negative sign indicates a current flowing away from the electrolyte). It should be appreciated that most of the current generated flows through electrode 106, rather than receiver 108, since receiver 108 exhibits a capacitive input impedance, at least in some embodiments. After $t_0$, but prior to $t_1$, $V_e$ exhibits several peaks with amplitude of the order of 4 mV. These peaks are the result of electrogenic activity in the cell. As illustrated, the amplitude of the peaks is significantly higher than the noise floor, thus making it easily detectable by receiver 108. The increase in the peaks of $V_e$ is due to a reduction in $R_{jm}$ when $I_e$ is set to −1 nA. Further sub-threshold signals are able to measured with the increased signal-to-noise ratio, in this example excitatory post synaptic potentials, which are unable to be resolved from the noise without the application of $I^e=-1$ nA. Of course, other values of $I_e$ other than −1 nA are also possible in other embodiments.

Figure 3D:
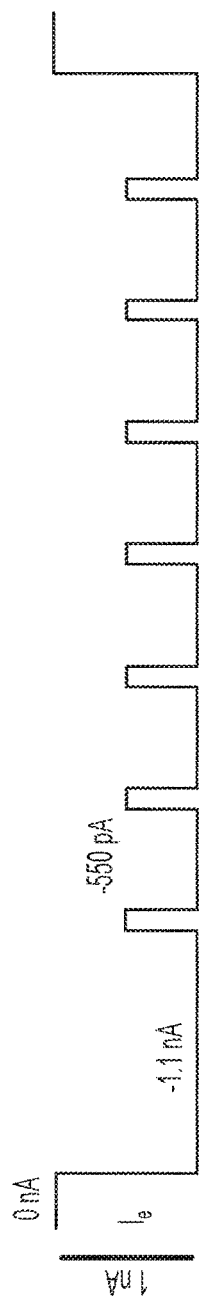
FIG. 3D is a plot illustrating a representative current for probing a cell, according to some non-limiting embodiments.
Figure 3E:
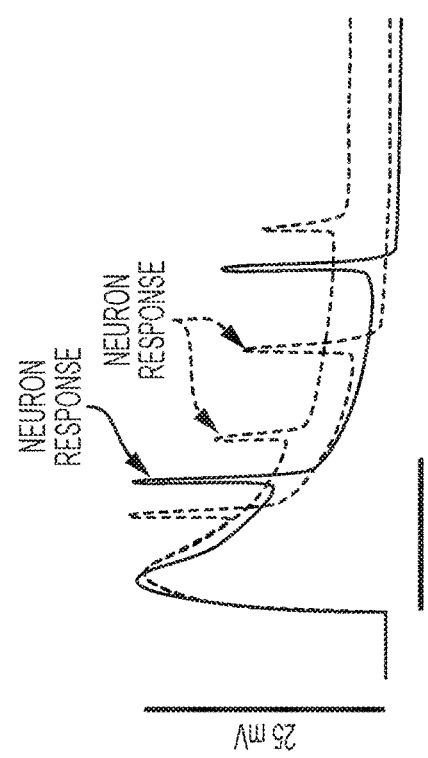
FIG. 3E is plot illustrating the voltage obtained when a cell is probed using the current of FIG. 3D, according to some non-limiting embodiments.

In some embodiments, to further enhance the cell's response, the stimulators may generate a first current value for reducing the value of $R_{jm}$, and subsequently a second current value for stimulating electrogenic activity. In some embodiments, the stimulator may alternate between the first and second current values, for example in a periodic fashion. An example of a current $I_e$ that may be generated to reduce resistance $R_{jm}$ and stimulate electrogenic activity is illustrated in the plot of FIG. 3D, in accordance with some embodiments. In this case, a −1.1 nA current is used to reduce $R_{jm}$, and a −550 pA is used to stimulate electrogenic activity. In response to such a current, voltage $V_e$ responds with the behavior of FIG. 3E. As shown, multiple peaks are generated in response to the −550 pA pulses. The peaks are the result of electrogenic activity within different cells. The peaks have amplitude of the order of 20 mV, thus significantly greater than those of FIG. 3C. It should be noted that voltage $V_e$ exhibits a decaying exponential characteristic owing to the fact that the electrode behaves with a low-pass response. The decaying exponential may be eliminated (or at least reduced) using a high-pass filter.

IV. Non-Limiting Examples of Stimulators

In some embodiments, impedance element 204 may be implemented as a switched capacitor. In some such embodiments, the magnitude of the current provided to the load may be set by setting the frequency output by frequency tuner 114.

IV.1 Basic Topology and Operating Principle

Figure 4A:
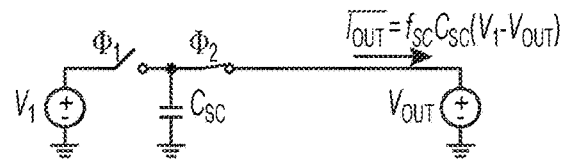
FIGS. 4A-4E are circuit diagrams of representative electrogenic stimulators, according to some non-limiting embodiments.

A capacitor $C_{SC}$ switched between DC voltages $V_1$ and $V_{OUT}$ ($V_1 > V_{OUT}$) with a non-overlapping two-phase ($\Phi_1$, $\Phi_2$) clock of frequency $f_{SC}$ (FIG. 4a) is equivalent to a resistor $R_{\textit{eff}} = 1/f_{SC}C_{SC}$ connecting the two DC voltages. The output current into the $V_{OUT}$ DC voltage source, averaged over a clock period, is given by $\overline{I_{OUT}} = f_{SC}C_{SC}(V_1 - V_{OUT})$. As $f_{SC}$ can be varied over many orders of magnitude, $\overline{I_{OUT}}$ can assume a wide range of values (with its minimum value being or example in the pA region). For example, with $C_{SC}$=30 fF, $V_1 - V_{OUT}$=0.6 V, and $f_{SC}$ increasing from 1 kHz by many orders of magnitude, $\overline{I_{OUT}}$ can be tuned up from 18 pA by the same orders of magnitude. Capacitor $C_{SC}$ and switches $\Phi_1$, $\Phi_2$ may serve as impedance element 204.

Figure 4B:
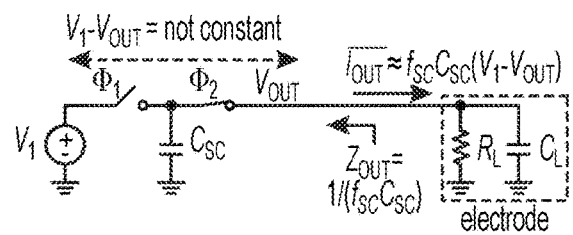

First, a case in which the switched capacitor drives the electrode immersed in an electrolyte (which is modeled as a Faradaic resistor $R_L$ in shunt with a double layer capacitor $C_L$) is considered (as in FIG. 4b). $V_{OUT}$ may not be constant and generally may vary as the current passes through the electrode, while $V_1$ may be still a DC voltage. $\overline{I_{OUT}}$ injected into the electrode can be still approximated as $\overline{I_{OUT}} \approx f_{SC}C_{SC}(V_1 - V_{OUT})$ but since $V_{OUT}$ varies with time, $\overline{I_{OUT}}$ may not be set at a constant value. In other words, as $\overline{I_{OUT}}$ linearly varies with $V_{OUT}$, the small-signal output resistance $Z_{OUT} = |\partial \overline{I_{OUT}} / \partial V_{OUT}|$ may be the same as the effective resistance of the switched capacitor, $R_{\textit{eff}}$. It should be appreciated that an infinite small-signal output resistance may be desired in current sources.

Figure 4C:
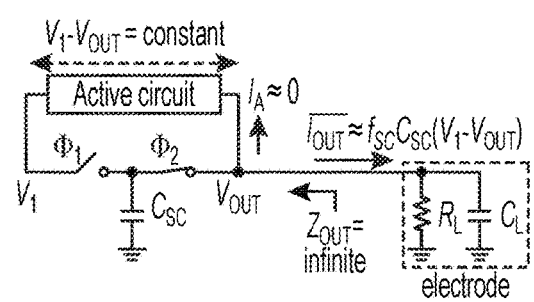

To promote a constant current, an active circuit (which may serve as the voltage follower 202$_1$ of FIG. 2) can be designed around the switched capacitor (FIG. 4c). If the active circuit achieves a constant $V_1 - V_{OUT}$ by making $V_1$ follow the change in $V_{OUT}$ and if it does not draw any appreciable current ($I_A \approx 0$), $\overline{I_{OUT}} \approx f_{SC}C_{SC}(V_1 - V_{OUT})$ may still hold and may be set at a desired constant by $f_{SC}$ and $C_{SC}$, independent of the generally changing $V_{OUT}$. This may result in an infinite $Z_{OUT}$.

Figure 4D:
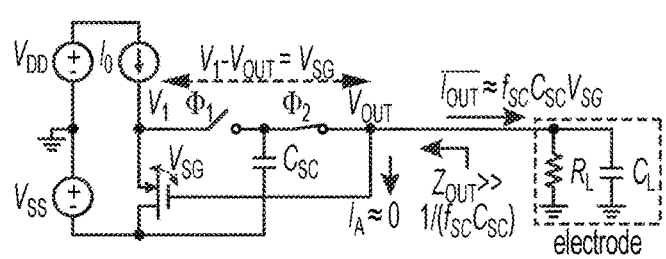

FIG. 4d shows one non-limiting embodiment of the switched-capacitor current stimulator of FIG. 4c, where a PMOS source follower serves as the active circuit. Of course, other types of transistors may be used in lieu of or in addition to the PMOS in some embodiments (e.g., an NMOS). The $V_1$ and $V_{OUT}$ nodes of the switched capacitor are connected to the source and gate of the PMOS transistor. $V_1$ thus follows the variation of $V_{OUT}$ with $V_1 - V_{OUT} = V_{SG}$, the source-gate voltage of the transistor. In the absence of transistor channel length modulation, $V_{SG}$ is set by the transistor parameters and its bias current $I_0$. Consequently, $V_1 - V_{OUT} = V_{SG}$ is a constant independent of $V_{OUT}$. At the same time, the source follower may draw a negligible current from the $V_{OUT}$ node due to the small gate capacitance of the PMOS transistor. Therefore, $\overline{I_{OUT}} \approx f_{SC}C_{SC}(V_1 - V_{OUT}) = f_{SC}C_{SC}V_{SG}$ is substantially independent of $V_{OUT}$ and can be set by $f_{SC}$ and $C_{SC}$ to a constant as needed.

Figure 4E:
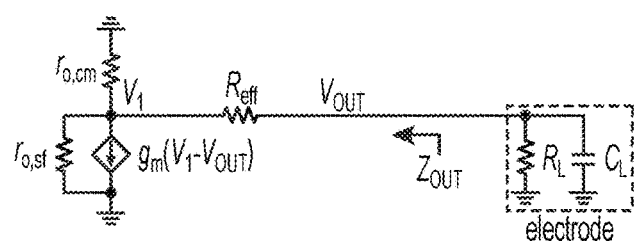

In the presence of transistor channel length modulation, $V_{SG}$ may vary with $V_{OUT}$ although it may do so with a weak dependence. Thus $\overline{I_{OUT}} \approx f_{SC}C_{SC}(V_1 - V_{OUT}) = f_{SC}C_{SC}V_{SG}$ may be well controlled, almost independent of $V_{OUT}$. The weak yet non-vanishing dependence of $\overline{I_{OUT}}$ on $V_{OUT}$ can be quantified by evaluating $Z_{OUT}$ with the small-signal model of FIG. 4e, where $r_{o,sf}$ and $r_{o,cm}$ are respectively the output resistances of the PMOS transistor and the current ($I_0$) bias circuit, and $g_m$ is the transconductance of the PMOS transistor:

$$Z_{OUT} = (r_{o,cm}r_{o,sf} + r_{o,cm}R_{\textit{eff}} + r_{o,sf}R_{\textit{eff}} + \quad (1)$$

$$g_m r_{o,cm} r_{o,sf} R_{\textit{eff}})/(r_{o,cm} + r_{o,sf})$$

$$\approx (g_m r_o/2) \times 1/(f_{SC}C_{SC}) + r_o/2.$$

Here the second line is approximated by setting $r_{o,sf} \approx r_{o,cm} \equiv r_o$ without losing essence and by using $g_m r_o \gg 1$. As seen, $Z_{OUT}$ may be boosted from the effective resistance $R_{\textit{eff}} = 1/f_{SC}C_{SC}$ of the switched capacitor by a factor of $g_m r_o/2$ (plus an extra term $r_o/2$). In the absence of transistor channel length modulation ($r_o = \infty$), $Z_{OUT} = \infty$. By way of example and not limitation, setting $g_m r_o/2 \sim 400$, may cause output current variation of only 0.3% across the output voltage range.

IV.2 Circuit Dynamics

In analysing the dynamics of the current stimulator of FIG. 4d, we first consider the capacitive load $C_L$ only ($R_L = \infty$) (Sec. IV.3) and then add the effect of the resistive load $R_L$ (Sec. IV.4). In this example, table I (FIG. 14a) summarizes the key time constants associated with the main signal path, along with associated capacitances and resistances. Of course, values other than those shown in table I may be used.

IV.3 Dynamics with $C_L$ Only ($R_L = \infty$)

Figure 5A:
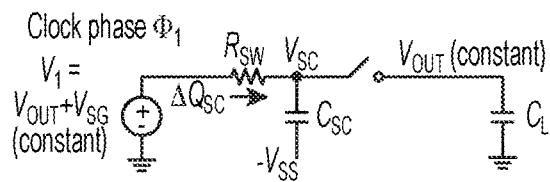
FIGS. 5A-5B are circuit diagrams of representative electrogenic stimulators, according to some non-limiting embodiments.

During the n-th clock phase $\Phi_1$ (n=1, 2, 3, . . . ), the switched capacitor may be disconnected from the $V_{OUT}$ node and connected to the $V_1$ node via the switch on-resistance, $R_{SW}$ (FIG. 5a). Throughout this $\Phi_1$ phase, $V_{OUT}$ may be at a constant value $\alpha_n$, and thus $V_1$ may be also maintained at a constant value $\alpha_n + V_{SG}$; in contrast, the switched capacitor voltage, $V_{SC}$, may exhibit a rapid upward transition from $V_{OUT} = \alpha_n$ to equalize with $V_1 = \alpha_n + V_{SG}$ (FIG. 5c), as $C_{SC}$ is charged with time constant $\tau_1 = R_{SW}C_{SC} < 1$ ns (Table I). This fast rise in $V_{SC}$ may occur in the very beginning of the $\Phi_1$ phase. After $V_{SC}$ settles, it may remain constant for the remainder of the $\Phi_1$ phase at $V_{SC} = V_1 = \alpha_n + V_{SG}$. The differential charge stored on $C_{SC}$ during this phase may be $\Delta Q_{SC} = C_{SC} \Delta V_{SC} = C_{SC} V_{SG}$.

Figure 5B:
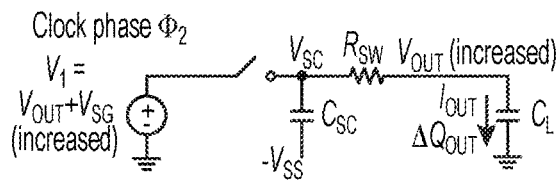
Figure 5C:
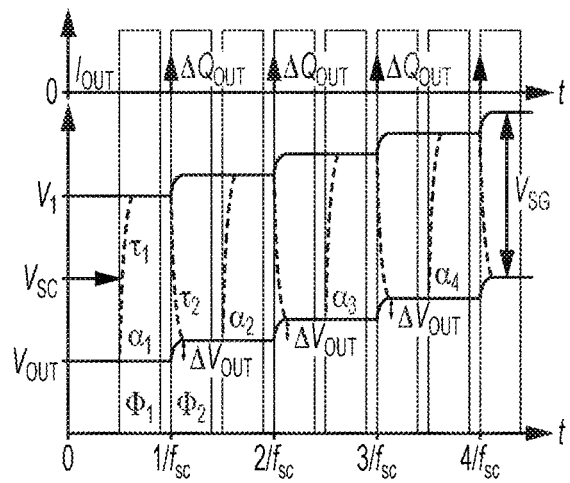
FIGS. 5C-5D are plots illustrating the behavior of the electrogenic stimulators of FIGS. 5A-5B, according to some non-limiting embodiments.
Figure 5D:
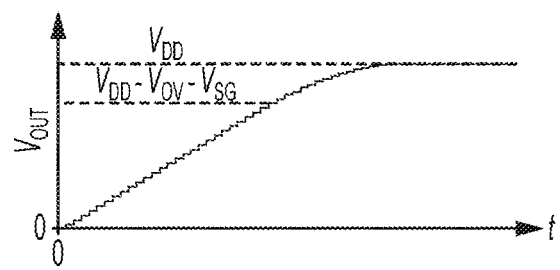

During the subsequent clock phase $\Phi_2$, the switched capacitor may be disconnected from the $V_1$ node and connected to the $V_{OUT}$ node via the switch on-resistance, $R_{SW}$ (FIG. 5b). This re-configuration may rapidly redistribute the differential charge $\Delta Q_{SC} = C_{SC}V_{SG}$ between $C_{SC}$ and $C_L$ with time constant $\tau_2 = R_{SW}C_L C_{SC}/(C_L + C_{SC}) \approx R_{SW}C_{SC} < 1$ ns (Table I; note $C_L \gg C_{SC}$), discharging $C_{SC}$ (lowering $V_{SC}$) and charging $C_L$ (raising $V_{OUT}$) until $V_{SC} = V_{OUT}$. Specifically, as shown in FIG. 5c, $V_{OUT}$ may rise from its initial value $\alpha_n$ to final value $\alpha_n + \Delta V_{OUT}$ where $$\Delta V_{OUT} = \Delta Q_{SC}/(C_{SC} + C_L) = C_{SC}V_{SG}/(C_{SC} + C_L) \approx \quad (2)$$
$$C_{SC}V_{SG}/C_L$$

while $V_{SC}$ may fall from its initial value $\alpha_n + V_{SG}$ to final value $\alpha_n + \Delta V_{OUT}$ ($V_1$ may follow the increase of $V_{OUT}$ to maintain the difference $V_{SG}$). These changes of $V_{SC}$ and $V_{OUT}$ may occur during the early part of the phase $\Phi_2$ due to the short time constant $\tau_2$, and all three voltages ($V_{SC}$, $V_{OUT}$ and $V_1$) may remain constant throughout the remainder of the phase $\Phi_2$. The charge packet injected to $C_L$ during the charge redistribution in the early part of $\Phi_2$ may be $\Delta Q_{OUT} = C_L \Delta V_{OUT}$. The output current $I_{OUT}$ driving $C_L$ may be due to this charge packet injection, and its average over a clock period may be given by $$\overline{I_{OUT}} = f_{SC} C_L \Delta V_{OUT} = f_{SC} C_{SC} V_{SG} \times [C_L/(C_{SC}+C_L)] \approx f_{SC} C_{SC} V_{SG}, \quad (3)$$

which is the expression introduced earlier. The process may be repeated at each clock cycle (FIG. 5c), and $V_{OUT}$ may rise in a staircase manner. After many clock cycles, $V_{OUT}$ may eventually start to roll off when $V_1$ becomes large enough to drive the current mirror transistor (not explicitly shown in the bias current ($I_0$) source of FIG. 4d) into the triode regime. Specifically, this $V_{OUT}$ roll-off may occur when $V_1 > V_{DD} - V_{OV}$ or when $V_{OUT} > V_{DD} - V_{OV} - V_{SG}$ where $V_{OV}$ is the overdrive voltage of the current mirror transistor (FIG. 5d). In this region, $V_{SG}$ may decrease leading to a corresponding decrease in $I_{OUT}$ due to Eq. (3) and $V_{OUT}$ may be eventually clipped at $V_{DD}$, at which point $I_{OUT}$ is diminished.

IV.4 Dynamics with $C_L$ and $R_L$

Figure 6A:
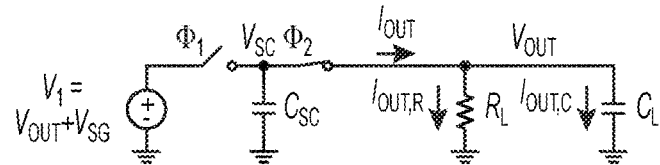
FIG. 6A is a circuit diagram of a representative electrogenic stimulator, according to some non-limiting embodiments.
Figure 6B:
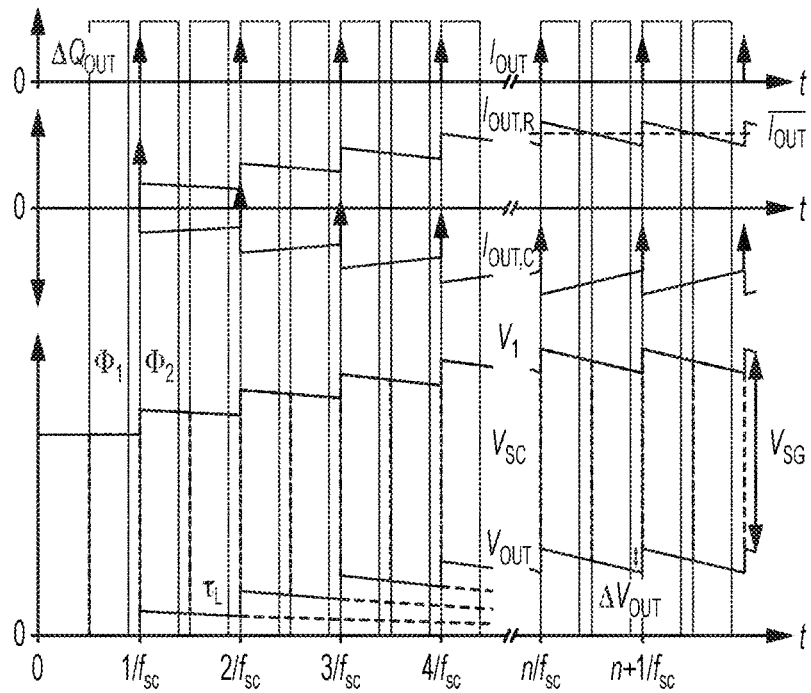
FIGS. 6B-6C are plots illustrating the behavior of the electrogenic stimulator of FIG. 6A, according to some non-limiting embodiments.

Next, a load having a resistive component $R_L$ in parallel with $C_L$ is considered (FIG. 6a). Since $R_L \gg R_{SW}$ and $C_L \gg C_{SC}$, the load's time constant $\tau_L = R_L C_L$ satisfies $\tau_L \gg \tau_1$, $\tau_2$ (Table I). Consequently, essentially the same rapid dynamics of the previous subsection may occur here too with time constant $\tau_1$ in phase $\Phi_1$ and with $\tau_2$ in phase $\Phi_2$, except that these fast dynamics may be overlaid with a decay of $V_{OUT}$, and therefore $V_1 = V_{OUT} + V_{SG}$, in the background due to the slow discharge of $C_L$ through $R_L$ with time constant $\tau_L$ (FIG. 6b, bottom). $V_{SC}$ may also exhibit a slow background decay with time constant $\tau_L$, equalized with $V_1$ during most of phase $\Phi_1$ (after a rapid upward transition from $V_{OUT}$ to $V_1$ with time constant $\tau_1$ in the beginning of $\Phi_1$) and equalized with $V_{OUT}$ during most of phase $\Phi_2$ (after a rapid downward transition from $V_1$ to $V_{OUT}$ with time constant $\tau_2$ in the beginning of $\Phi_2$).

With repeated clock cycles $V_{OUT}$ may be a sequence of a rapid $\Delta V_{OUT}$ up-step (time constant $\tau_2$) followed by a slow decay (time constant $\tau_L$): see FIG. 6b, bottom. Here $\Delta V_{OUT}$ in the beginning of each clock phase $\Phi_2$ may be again by Eq. (2). Therefore, $I_{OUT}$ injected into the electrode corresponds to the charge packet $\Delta Q_{OUT} C_L \Delta V_{OUT}$ injected into $C_L$, and thus $\overline{I_{OUT}}$ may remain the same as Eq. (3) (FIG. 6b, top). If we break down $I_{OUT}$ into current $I_{OUT,R}$ through $R_L$ and current $I_{OUT,C}$ through $C_L$ ($I_{OUT} = I_{OUT,R} + I_{OUT,C}$) in phase $\Phi_2$, the rapid charging of $C_L$ in the beginning of the phase may be described by $I_{OUT} \approx I_{OUT,C} > 0$, while the background slow discharging of $C_L$ through $R_L$ maybe described by $-I_{OUT,C} \approx I_{OUT,R}$ ($I_{OUT,C} < 0$) with $I_{OUT} \approx 0$ (FIG. 6b, top and middle).

Figure 6C:
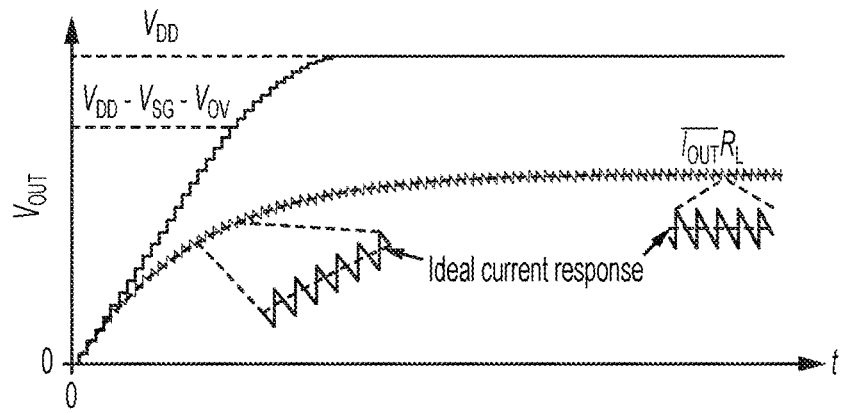

In the initial clock cycles, the charging of $C_L$ by the charge packet injection $\Delta Q_{OUT} = C_L \Delta V_{OUT}$ per clock cycle may exceed its discharging through $R_L$ per clock cycle thus $V_{OUT}$ may rise, but once $C_L$ is sufficiently charged at later clock cycles, its charging and discharging may balance each other, and $V_{OUT}$ may reach a plateau (except ripples) (FIG. 6b, bottom; FIG. 6c). This evolution of $V_{OUT}$ into the steady state (neglecting the ripples) can be quantified by evaluating $V_{OUT}$ at $t = n/f_{SC}$ or at the end of n-th clock phase $\Phi_2$ as follows, $$V_{OUT}(t) = \Delta V_{OUT} \sum_{k=1}^{n} \exp\left(-\frac{k}{f_{SC} R_L C_L}\right) \times \left(-\frac{1}{2f_{SC} R_L C_L}\right) \approx \quad (4)$$

$$\overline{I_{OUT}} R_L \left[1 - \exp\left(-\frac{t}{R_L C_L}\right)\right],$$

where $f_{SC} \tau_L = f_{SC} R_L C_L \gg 1$. $\Delta V_{OUT}$ may converge to $\overline{I_{OUT}} R_L$ in steady state (FIG. 6c). This is equivalent to flowing $\overline{I_{OUT}}$ into the electrolyte through the resistance $R_L$. In fact, the overall voltage response of the $R_L C_L$ load to the switched-capacitor current stimulator captured by Eq. (4) (ignoring the ripples) may be the same as the voltage response of the $R_L C_L$ load to an ideal step current with a magnitude $\overline{I_{OUT}}$ (FIG. 6c).

As such, the current stimulator may be viewed, at least in some embodiments, as a source of constant current (or at least, substantially constant). At least in some biological applications, the biological tissue may have RC time constants $\approx 1$ ms, which will smoothen the high frequency ripples. It should be appreciate that, while resistance $R_L$ has been assumed as a constant in the analysis above, it may be a function of the current in some embodiments.

While the foregoing discussion has assumed $\overline{I_{OUT}} R_L < V_{DD} - V_{OV} - V_{SG}$, this need not necessarily be the case in all embodiments; if $\overline{I_{OUT}} R_L > V_{DD} - V_{OV} - V_{SG}$, $V_{OUT}$ may roll off and be clipped at $V_{DD}$ instead of saturating to $\overline{I_{OUT}} R_L$.

IV.5 Representative Implementation

Figure 7A:
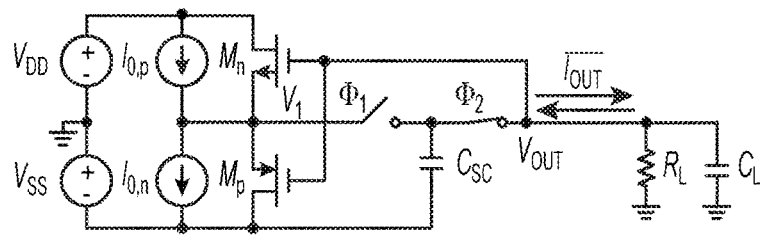
FIGS. 7A-7C are circuit diagrams of representative biphasic electrogenic stimulators, according to some non-limiting embodiments.
Figure 7B:
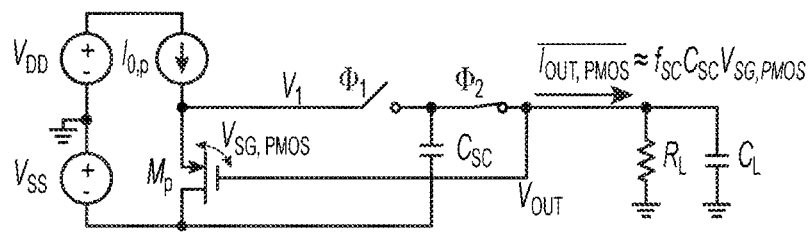
Figure 7C:
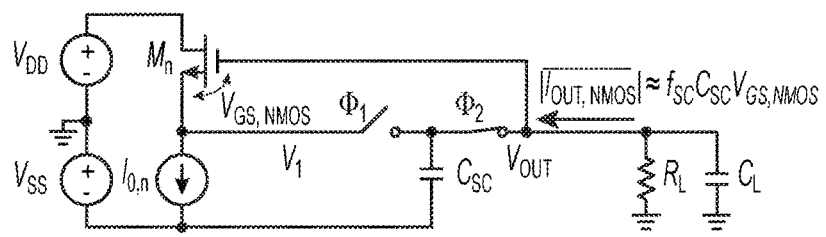

Some embodiments are directed to biphasic stimulators, which may be configured to drive current towards the cells and/or away from the cells. A representative biphasic stimulator is illustrated in FIGS. 7a-7c. In this configuration, transistor $M_n$ (NMOS) may serve as voltage follower $202_1$ and transistor $M_p$ (PMOS) may serve as voltage follower $202_2$. These biphasic stimulators allow for control of the current polarity by turning on either current source $I_{0,p}$ or $I_{0,n}$. For example, with $I_{0,p}$ on and $I_{0,n}$ off, only PMOS transistor $M_p$ is activated (FIG. 7b); in this regime, the PMOS source follower around the switched capacitor may set $V_1 - V_{OUT} = V_{SG,PMOS} > 0$, thus enabling the switched capacitor to inject a positive current $\overline{I_{OUT,PMOS}} \approx f_{SC} C_{SC} V_{SG,PMOS} > 0$. On the other hand, with $I_{0,n}$ on and $I_{0,p}$ off, only NMOS transistor $M_n$ is activated (FIG. 7c). The NMOS source follower around the switched capacitor may set $V_1 - V_{OUT} = -V_{GS,NMOS} < 0$, injecting a negative current $\overline{I_{OUT,NMOS}} \approx -f_{SC} C_{SC} V_{GS,NMOS} < 0$. It should be appreciated that, while the illustrated implementation uses a PMOS transistor to drive current in one direction and an NMOS transistor to drive current in the other direction, other arrangements are also possible.

Figure 7D:
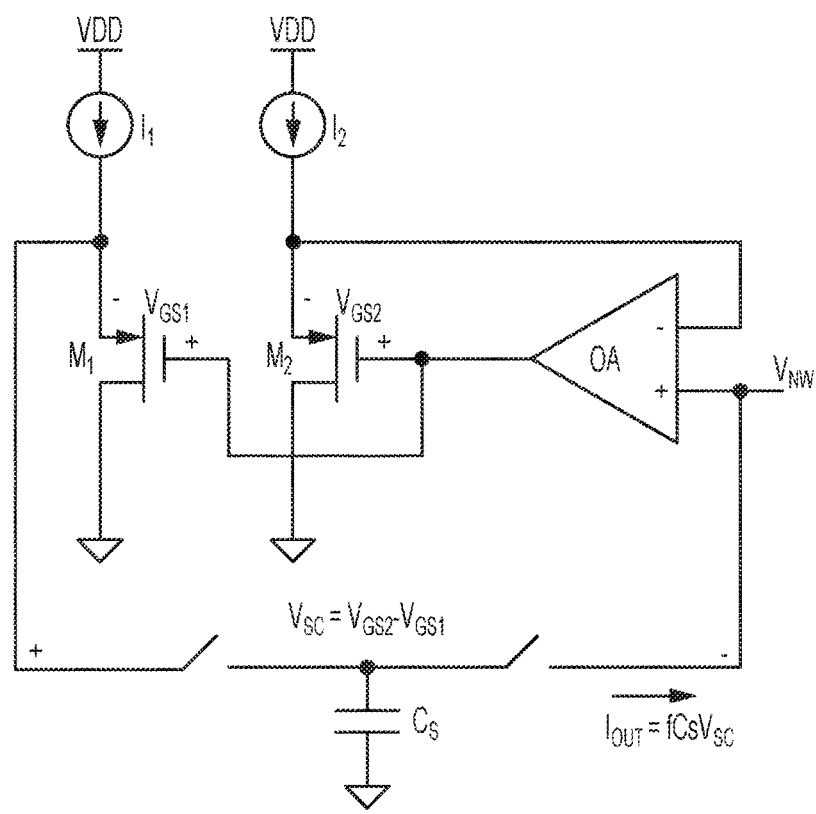
FIG. 7D is a circuit diagram illustrating a representative electrogenic stimulator including an operational amplifier, according to some non-limiting embodiments.

In some embodiments, current-based stimulators may be implemented using operational amplifiers. FIG. 7D illustrates an example of a stimulator including an operational amplifier. In this case, operational amplifier OA control the operations of transistors $M_1$ and $M_2$, which are arranged as voltage followers. Switched capacitor Cs serves as the impedance element. The output current $I_{out}$ delivered by the stimulator of FIG. 7D is proportional to the switching frequency f, the capacitance Cs and the voltage across the switches $V_{SC}$. Because $V_{SC}$ is set by the difference between $V_{GS2}$ and $V_{GS1}$ (which in turn may depend upon currents $I_2$ and $I_1$), this stimulator is able, at least in some embodiments, to deliver currents of less than 1 pA, when needed.

The inventors have appreciated that at least some of the electrogenic stimulators described herein may suffer from voltage ripples, as shown for example in FIG. 6C. In some circumstances, these voltage ripples may couple to and potentially negatively affect the operations of a receiver 108. In some embodiments, coupling of the voltage ripples to a receiver may be limited, or even eliminated, by 1) providing a sufficiently high frequency (e.g., greater than 1 MHz) to the switched capacitor serving as the impedance element, and 2) including a high-frequency cutting filter (e.g., a low-pass filter or a band-pass filter) having a sufficiently low cut-off frequency (less than the frequency driving the switched capacitor) in a receivers 108. In this way, the voltage ripples are blocked by the filter, and do not reach the receiver 108.

Figure 7E:
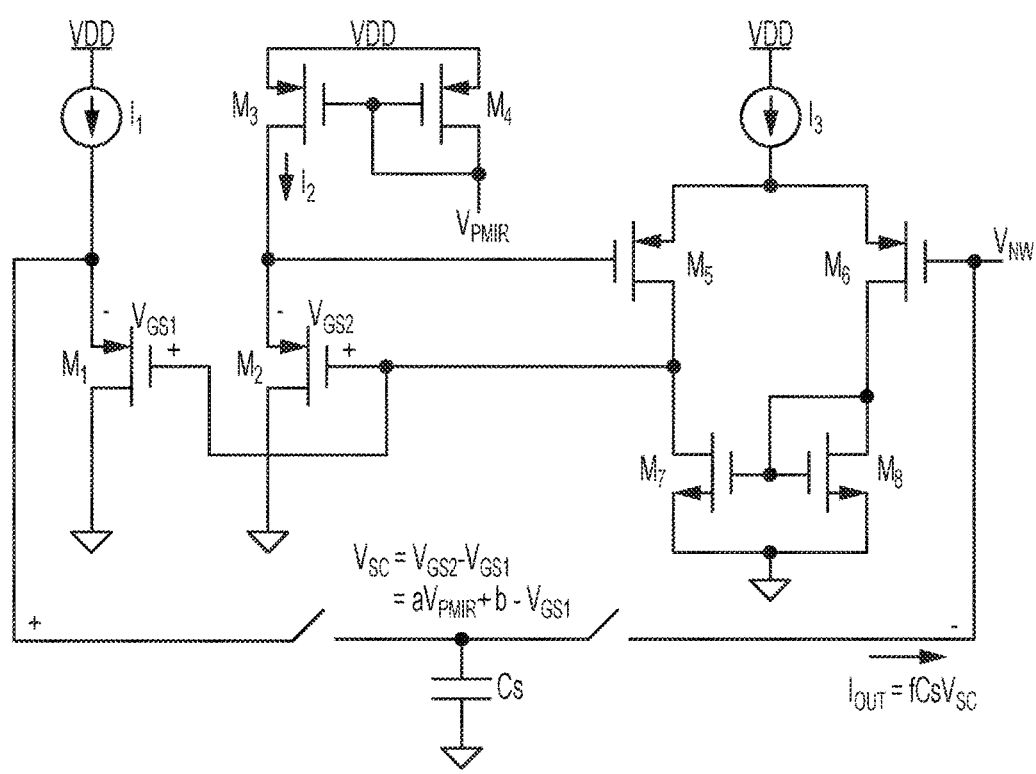
FIG. 7E is a circuit diagram illustrating a representative electrogenic stimulator arranged to limit voltage ripples, according to some non-limiting embodiments.

In some embodiments, the operational amplifier may be added to further reduce the effect of the ripples at the receiver. By including an operational amplifier in the current stimulator, the input frequency can be significantly increased to values above the cut-off frequency of the receiver filter. This is because, using the operational amplifier, the voltage $V_{SC}$ (and thus $I_{out}$) can be increased without having to necessarily increase the frequency f. In this way, the frequency f can be kept outside the band of the filter, thus suppressing the noise frequency. FIG. 7E illustrates another example of a current-based stimulator including an operational amplifier, according to some embodiments. In this case, transistors $M_5$, $M_6$, $M_7$ and $M_8$ serve as operational amplifier OA, and transistors $M_1$ and $M_2$ set the voltage $V_{SC}$ $V_{GS2}$-$V_{GS1}$. In this case, the value of $V_{GS2}$ can be set based on $V_{PMIR}$. By keeping $I_1$ constant and adjust $I_2$ through $V_{PMIR}$, any suitable value of $V_{SC}$ can be obtained, thus providing a continuous tunability on the output current $I_{out}$.

Figure 8:
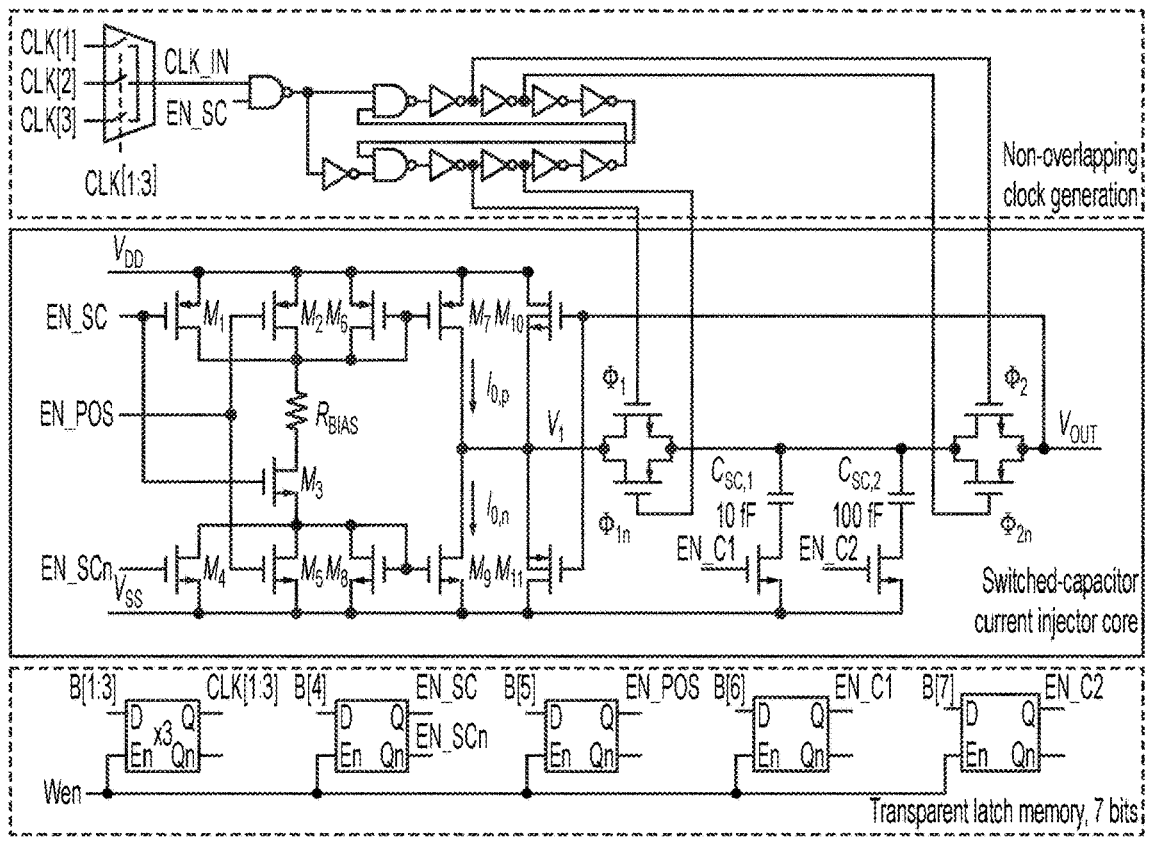
FIG. 8 is a circuit diagram illustrating a representative system for stimulating electrogenic cells, according to some non-limiting embodiments.

The middle of FIG. 8 (solid box) shows a representative transistor-level schematic of the circuit of FIG. 7a. In this example, the core switched capacitor circuit uses two transmission gates and allows for the option of a 10 fF or 100 fF switched capacitance (control signals: EN_C1, EN_C2). Transistors $M_{10}$ and $M_{11}$, corresponding to $M_n$ and $M_p$ of FIG. 7a, are the complementary source follower transistors. As discussed above, channel length modulation may partially degrade the source following behavior, by rendering $|V_{SG}|$ of transistors $M_{10}$ and $M_{11}$ weakly dependent on $V_{OUT}$.

The inventors have appreciated that the body effect can further weaken, at least in some embodiments, the source following behavior by increasing the $|V_{SG}|$ dependency on $V_{OUT}$. As such, the body effect is limited, at least in some embodiments, by connecting the source and body terminals not only in the PMOS transistor $M_{11}$ but also in the NMOS transistor $M_{10}$; while such body-source connection is often not possible for NMOS transistors, some CMOS technologies allow for triple-well NMOS transistors, which in turn allows for the source-body connection at the expense of increased transistor area.

Transistors $M_1$-$M_9$ together with resistor $R_{BIAS}$ (~750 kΩ in this example) may form a current bias network that realizes the $I_{0,p}$ and $I_{0,n}$ current sources of FIG. 7a. The $M_1$-$M_5$ network with $R_{BIAS}$ may set the reference current that is mirrored as $I_{0,p}$ by the PMOS pair $M_6$-$M_7$ and as $I_{0,n}$ by the NMOS pair $M_8$-$M_9$. In this bias network, either the PMOS mirror $M_6$-$M_7$ or the NMOS mirror $M_8$-$M_9$ is active (control signal: EN_POS) so that the overall circuit can work in either positive or negative injection mode, as explained in connection with FIG. 7 (the bias network can also be turned off entirely by using the control signal EN_SC). In this case, $I_{0,n}$=$I_{0,p}$=~3 μA and $|V_{SG}|$~0.6 V for both $M_{10}$ and $M_{11}$. The theoretical maximum output current $|\overline{I_{OUTMAX}}|$ may be ~1.5 μA, the half of $I_{0,n}$=$I_{0,p}$=~3 μA, due to symmetric 50% duty cycle clock phases, $\Phi_1$ and $\Phi_2$ (FIG. 8, top). Furthermore, the clock phases $\Phi_1$ and $\Phi_2$ may be non-overlapping to prevent shoot through from $V_1$ to $V_{OUT}$. The master clock, CLK_IN can be selected from three clock inputs, CLK[1:3], thus enabling flexible control of $f_{SC}$. All control signals may be stored locally or controlled externally through a n-bit (7-bit in the example of FIG. 8) transparent latch memory.

In the non-limiting example in which $V_{DD}$=1.8 V and $V_{SS}$=−1.8 V, $|V_{SG}|$~0.6 V for $M_{10}$ and $M_{11}$, $I_{OUT}$ may be nearly constant with only 0.3% simulated variation for $V_{OUT}$ within ±1.2 V for biphasic stimulation. By varying $f_{SC}$ between 1 kHz, which is near the high frequency cutoff of typical electrogenic cells, and 10 MHz, $|\overline{I_{OUT}}|$ of Eq. (3) is varied from 6 pA to 60 nA for $C_{SC}$=10 fF and from 60 pA to 0.6 μA for $C_{SC}$=100 fF. This range of $|\overline{I_{OUT}}|$ can cover both intracellular and extracellular stimulation. The ripple voltage $\Delta V_{OUT}$ of Eq. (2) varies, in this example, from 0.6 mV to 60 mV depending on $C_{SC}$ and $C_L$ (Table I). This $\Delta V_{OUT}$ is much less than typical stimulation voltages on the order of 0.1~1 V and would be averaged out by the RC network of the cells.

Figure 9:
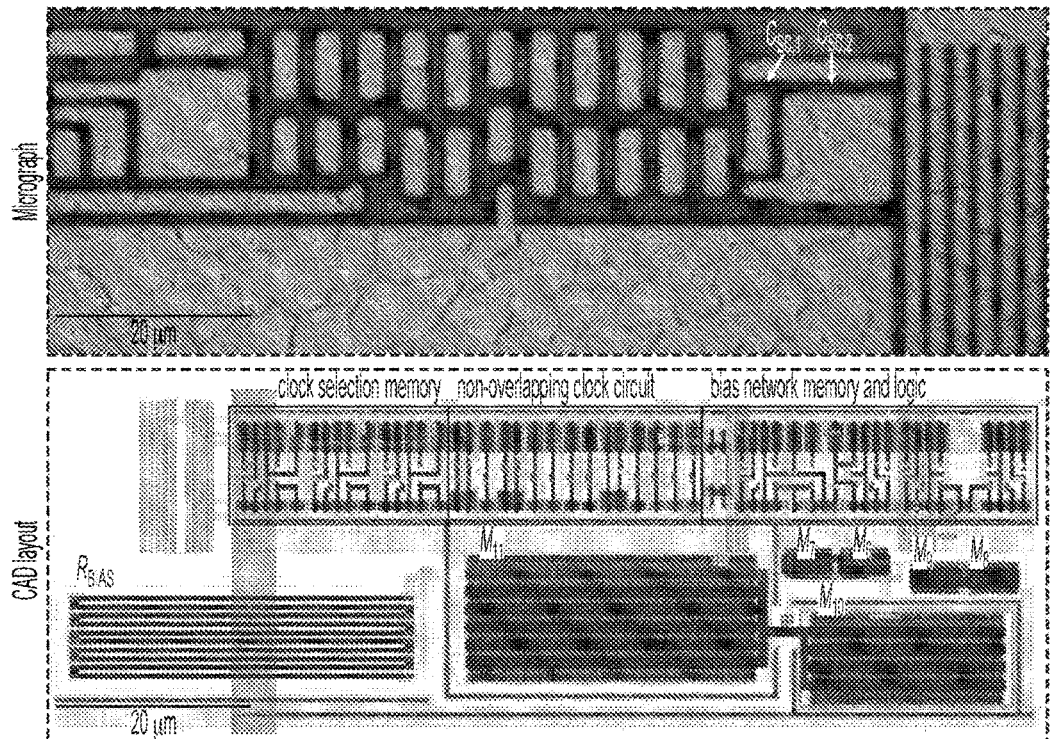
FIG. 9 is a layout illustrating a representative system for stimulating electrogenic cells, according to some non-limiting embodiments.

The circuit of FIG. 8 was fabricated in a 0.18 m-CMOS technology (FIG. 9) in an active area of only 0.003 mm². The memories, 7 bits in total, and logic occupy ~0.001 mm², current mirrors and source followers ~0.001 mm², bias resistor ~0.0004 mm², and the 10 fF and 100 fF capacitors of the standard MIM structure on the top metal layer together ~0.0002 mm².

IV.6 Experimental Results

Figure 10A:
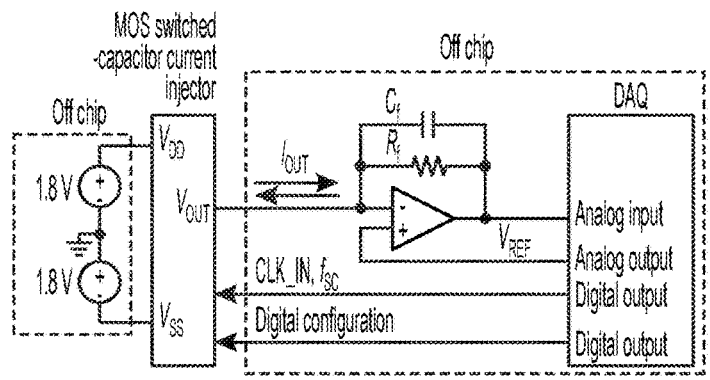
FIG. 10A is a circuit diagram illustrating a representative experimental setup for stimulating electrogenic cells, according to some non-limiting embodiments.

The circuit of FIG. 8 was characterized by measuring $\overline{I_{OUT}}$ of the current stimulator when $V_{OUT}$ is fixed to a variable DC voltage $V_{REF}$ (which may be an input to an off-chip operational amplifier in a negative feedback and may set by a data acquisition (DAQ) card) (FIG. 10a). The negative feedback loop of the operational amplifier comprises in the example a parallel $R_f C_f$ network with either ($R_f$, $C_f$)=(100 MΩ, 10 pF) or ($R_f$, $C_f$)=(10 MΩ, 100 pF). Either of these transimpedance operational amplifiers configurations has a bandwidth of 100 Hz and thus is configured to average out the ripples in $I_{OUT}$. The second set of $R_f$ and $C_f$ values may be configured to limit the voltage drop across the negative feedback path when $\overline{I_{OUT}}$ is large.

Figure 10B:
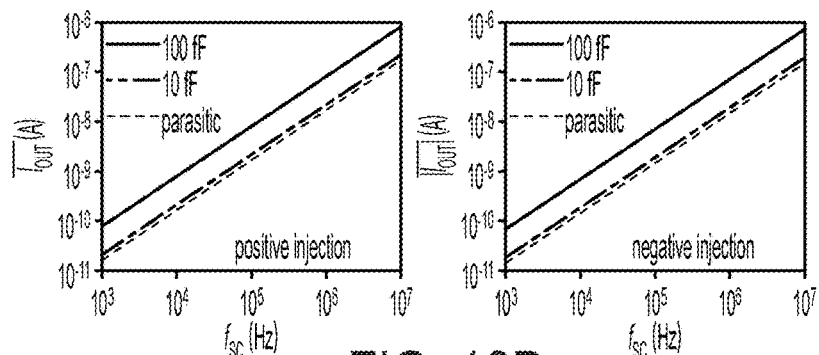
FIGS. 10B-10D are plots illustrating the behavior of the circuit of FIG. 10A, according to some non-limiting embodiments.

FIG. 10b shows the measured positive and negative $\overline{I_{OUT}}$ vs. $f_{SC}$ swept from 1 kHz to 10 MHz for $V_{OUT}$=$V_{REF}$=0 V. As illustrated, $|\overline{I_{OUT}}|$ exhibits a linear dependence relative to $f_{SC}$ over the four decades of frequency. By fitting these curves, the following parameters can be extracted: $V_{SG,PMOS}$=0.63 V, $V_{GS,NMOS}$=0.56 V, and a parasitic capacitance $C_p$ of 26 fF in shunt with the two alternate switched capacitances of 10 fF and 100 fF. In this case, the minimum $|\overline{I_{OUT}}|$ is ~20 pA at $f_{SC}$=1 kHz with $C_{SC}$=10 fF and $C_p$=26 fF and the maximum $|\overline{I_{OUT}}|$ is ~0.7 μA at $f_{SC}$=10 MHz with $C_{sc}$=100 fF and $C_p$=26 fF.

Figure 10C:
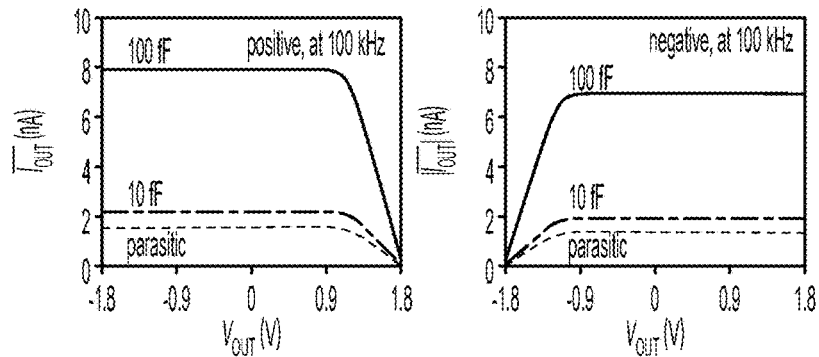
Figure 10D:
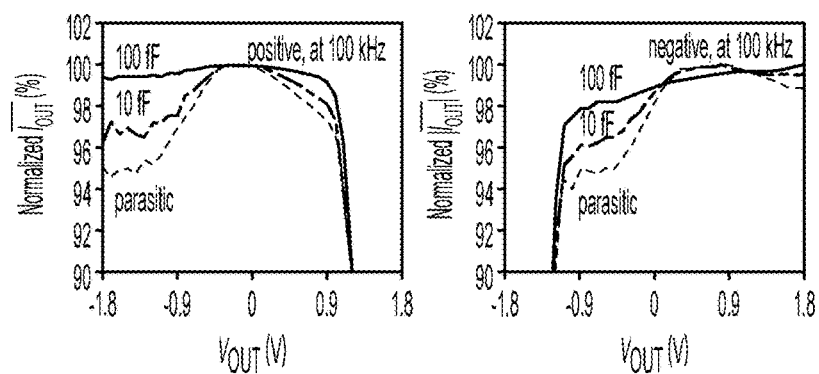

To demonstrate the weak dependence of $\overline{I_{OUT}}$ on $V_{OUT}$ for a given frequency, $V_{OUT}$=$V_{REF}$ is swept from −1.8 V to 1.8 V while fixing $f_{SC}$ at 100 kHz. The positive $\overline{I_{OUT}}$ shows a flat response for $V_{OUT}$ between −1.8 V and 1.2 V and rolls off outside of this range; the negative $\overline{I_{OUT}}$ shows a flat response between −1.2 V and 1.8 V and rolls off outside of this range (FIG. 10c). This demonstrates that the $V_{OUT}$ range for biphasic stimulation is ±1.2 V as expected. Furthermore, the measured variations of $|\overline{I_{OUT}}|$ in the flat regions are within ~4% for $C_{SC}$=10 fF and even less for $C_{SC}$=100 fF (FIG. 10d). Given the smaller variation of $C_{SC}$=100 fF compared to $C_{SC}$=10 fF and the similarity of the voltage dependence for both positive and negative injections, the observed max ~4% variations of $\overline{I_{OUT}}$ with $V_{OUT}$, which is larger than the theoretical 0.3%, are mainly attributed to the voltage dependence of the parasitic capacitance. Nonetheless, even the measured 4% of current variation may be sufficient in most biological applications. In addition, the observed variations of $\overline{I_{OUT}}$ with $V_{OUT}$ remains substantially the same when $f_{SC}$ is swept from 1 kHz to 10 MHz due to $Z_{OUT}$'s direct dependence on $I_{OUT}$.

Figure 11:
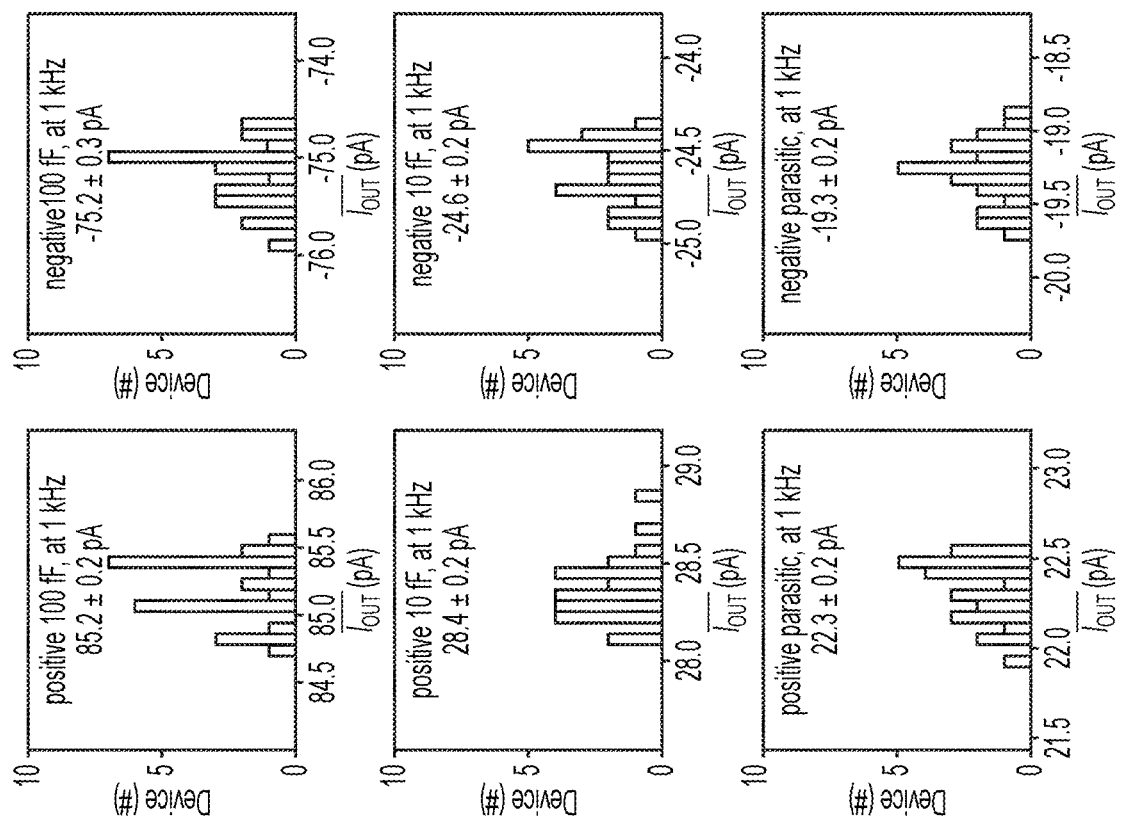
FIG. 11 illustrates a plurality of plots representing the current response of the circuit of FIG. 10A, according to some non-limiting embodiments.

The same line of measurements of FIG. 10 was repeated across 25 different circuits to examine the variability. Results with $f_{SC}$=1 kHz are displayed in FIG. 11. The $\overline{I_{OUT}}$ averaged over the 25 devices is slightly increased relative to FIG. 10, because the measurements of FIG. 11 were performed after post-fabrication of platinum electrodes on the chip surface for the later characterization in electrolyte, which increased the parasitic capacitance of the MIM switched capacitors located near the surface. However, the chip-to-chip variations—whose evaluation is the key goal of the FIG. 11 measurements-exhibit a standard deviation of ~1.0% for both positive and negative $\overline{I_{OUT}}$: this variability is due to process-dependent $|V_{GS}|$, $C_{SC}$, and parasitic capacitance.

Figure 12A:
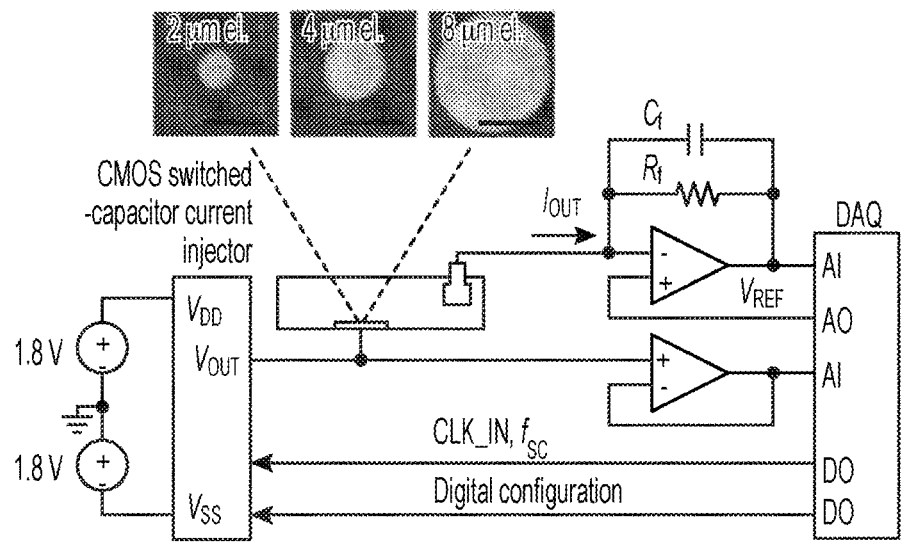
FIG. 12A is a circuit diagram illustrating another representative experimental setup for stimulating electrogenic cells, according to some non-limiting embodiments.

The CMOS current stimulator was characterized with varying size of electrodes immersed in a salt solution containing NaCl (119 mM), KCl (5 mM), HEPES (20 mM), $CaCl_2$ (2 mM), $MgCl_2$ (2 mM), glucose (30 mM) and glycine (0.001 mM). FIG. 12a shows the measurement setup. Three current stimulator circuits are used, where the $V_{OUT}$ of each circuit is connected to an open pad on the top-most metal layer. Circular platinum electrodes are post-fabricated on the surface by first depositing Pt onto the open pads and subsequently depositing an insulating ~500 nm of $SiO_2$. Circular regions of Pt with diameters of 2 μm, 4 μm, and 8 μm are then selectively etched open. The theoretical capacitance, $C_L$, of these 2 μm, 4 μm, and 8 μm Pt electrodes are 1.7 pF, 6.8 pF, and 27 pF, respectively, with voltage dependent Faradaic resistances $R_L$, on the order of ~50 MΩ to ~2 GΩ. Polydimethylsiloxane (PDMS) microfluidic wells are attached to contain the salt solution. A DC input $V_{REF}$ to an off-chip transimpedance op-amp with a 100-Hz bandwidth is connected to an Ag/AgCl reference electrode to bias the salt solution at $V_{REF}$=−0.2 V, which initializes the bias for $V_{OUT}$ approximately at 0 V in the middle between $V_{DD}$=1.8 V and $V_{SS}$=−1.8 V, with the difference between $V_{OUT}$ and $V_{REF}$ arising from the built-in potential of the electrode. The current measured through the reference electrode is the same as $I_{OUT}$. An additional op-amp buffer is used to measure $V_{OUT}$, sampling it at 100 kHz.

Figure 12B:
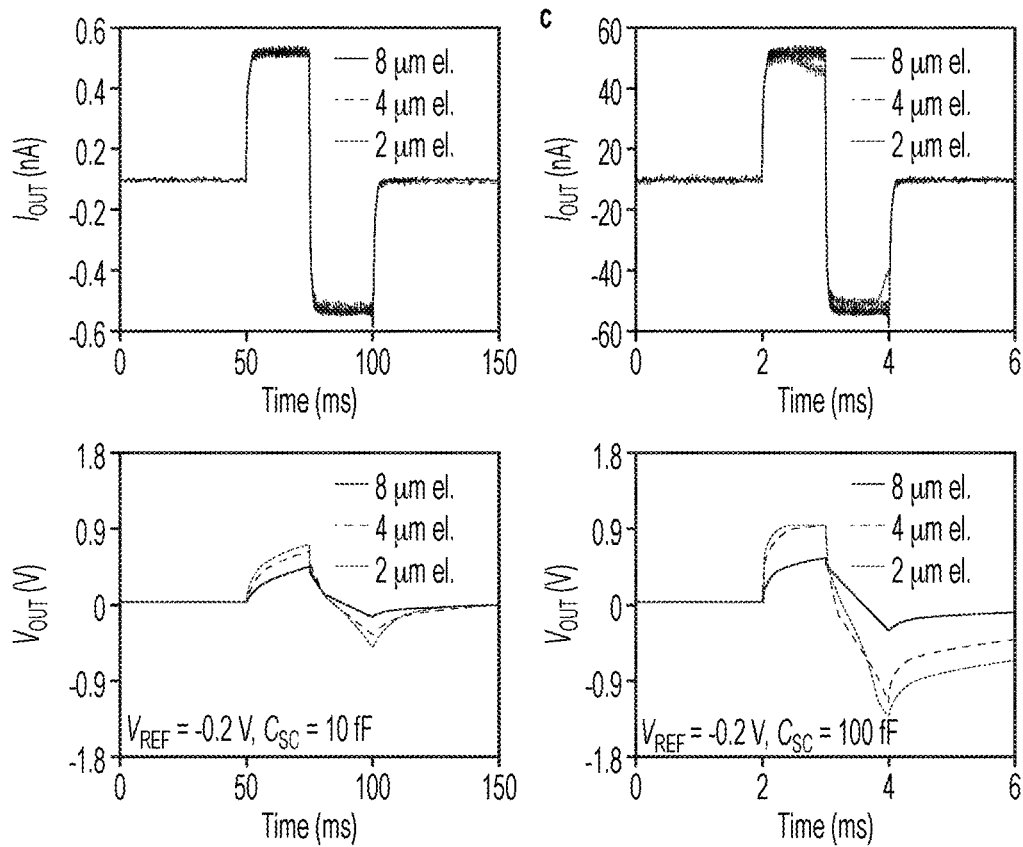
FIGS. 12B-12C are plots illustrating the behavior of the circuit of FIG. 12A, according to some non-limiting embodiments.

The parameters of the three circuits—such as $f_{SC}$—are adjusted through the DAQ card to produce an equal magnitude (500 pA) of positive and negative currents (FIG. 12b). As a result, a 500-pA constant amplitude biphasic current pulse with a pulse duration of 50 ms is injected through each electrode. This injection of constant $|I_{OUT}|$ measured through the platinum and reference electrode (FIG. 12b, top)—which is averaged by the transimpedance op-amp and thus can be regarded as $|\overline{I_{OUT}}|$—occurs while the measured $V_{OUT}$ rises (FIG. 12b, bottom).

Figure 12C:

A 50 nA, 2-ms duration biphasic pulse is then injected to mimic an extracellular stimulation (FIG. 12c; for this higher pulse rate with the larger current magnitude, $R_f$=10 MΩ in parallel with $C_f$=100 pF is used for the transimpedance op-amp with two subsequent high-frequency boost circuits to extend the measurement bandwidth to ~10 kHz). With this larger $|\overline{I_{OUT}}|$ injection, the circuit with the 8-μm diameter electrode shows the same behavior as in FIG. 12b with no reduction in $|\overline{I_{OUT}}|$ thanks to the relatively smaller $R_L$. In contrast, for the two circuits with the 4-μm and 2-μm diameter electrodes with relatively larger $R_L$'s, $|\overline{I_{OUT}}|$ is reduced (FIG. 12c, top) due to $V_{OUT}$ entering the regions of $|V_{OUT}|$>1.2 V, as expected (FIG. 12c, bottom; the measured high-end $V_{OUT}$ is clipped at ~0.9 V due to the saturation of the op-amp buffer).

Figure 13:
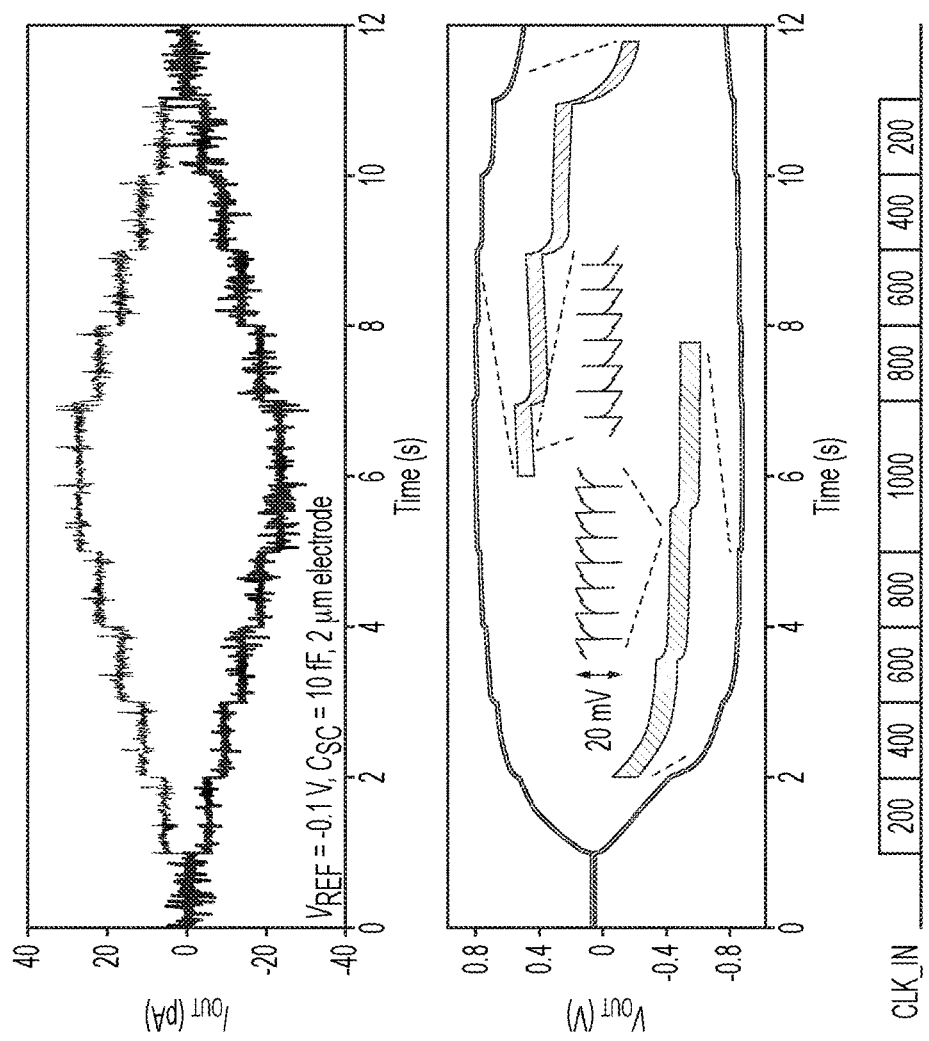
FIG. 13 illustrates plots representing the current and voltage response of the circuit of FIG. 12A, according to some non-limiting embodiments.

The measurements of FIG. 13 are done with the same setup as in FIG. 12a and highlight the small amplitude current injection using the 2-μm diameter electrode immersed in the salt solution. $f_{SC}$ is increased from 0 Hz to 1 kHz and then decreased back to 0 Hz, in 200 Hz increments. This results in ~5 μA step current increases/decreases for positive/negative injections (FIG. 13, top). For these measurements, the transimpedance op-amp circuit of FIG. 12a uses $R_f$=10 MΩ and $C_f$=100 pF but without high-frequency boost circuits; a moving window average having a window size of 10 ms is used to minimize the measurement noise. The positive current injection (top waveform in FIG. 13) reaches a maximum of 28 pA while the negative injection (bottom waveform) reaches a minimum of −25 pA. The ripple voltage can be seen (FIG. 13, middle), with ~20 mV step size for both positive and negative injections.

Table II (FIG. 14b) summarizes the results obtained in the characterization described above.

It should be appreciated that the parameters provided in Table I are only representative, as other values may be used. For example, $R_{SW}$ may be between 1Ω and 10 kΩ, $C_{SC}$ may be between 0.1 fF and 10 nF, $C_L$ may be between 1 fF and 10 nF, $R_L$ may be between 1 kΩ and 100 GΩ, $\tau_1$ may be between 1 ps and 10 ns, $\tau_2$ may be between 1 ps and 10 ns, and $\tau_L$ may be between 100 ns and 10 ms. It should be further appreciated that not all embodiment are limited to $C_L \gg C_{SC}$, $R_L \gg R_{SW}$, and/or $\tau_L \gg \tau_1, \tau_2$.

V. Electrode Design

In some embodiments, the electrodes $106_1, 106_2 \ldots 106_N$ may be shaped as nanowires or as pluralities of nanowires. One example of an electrode being shaped as a plurality of nanowires is depicted in FIG. 15A, where a cell 104 is brought into contact with a substrate 1520 having an array of vertical nanowires 1530. The substrate may be planar or substantially planar in some embodiments. One or more of the ends 1540 of nanowires 1530 may be inserted into cell 104. As discussed herein, some or all of the nanowires may be individually addressable, e.g., for recording and/or for applying an electrical force to the cell. Nanowires that may be used can be formed of material with low cytotoxicity, such as silicon, silicon oxide, silicon nitride, silicon carbide, iron oxide, aluminum oxide, iridium oxide, tungsten, stainless steel, silver, platinum, and gold. Other suitable materials include aluminum, copper, molybdenum, tantalum, titanium, nickel, tungsten, chromium, or palladium. In some embodiments, the nanowire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanowires as the semiconductor, for example, gallium arsenide, gallium nitride, indium phosphide, cadmium selenide, etc.

Figure 15C:
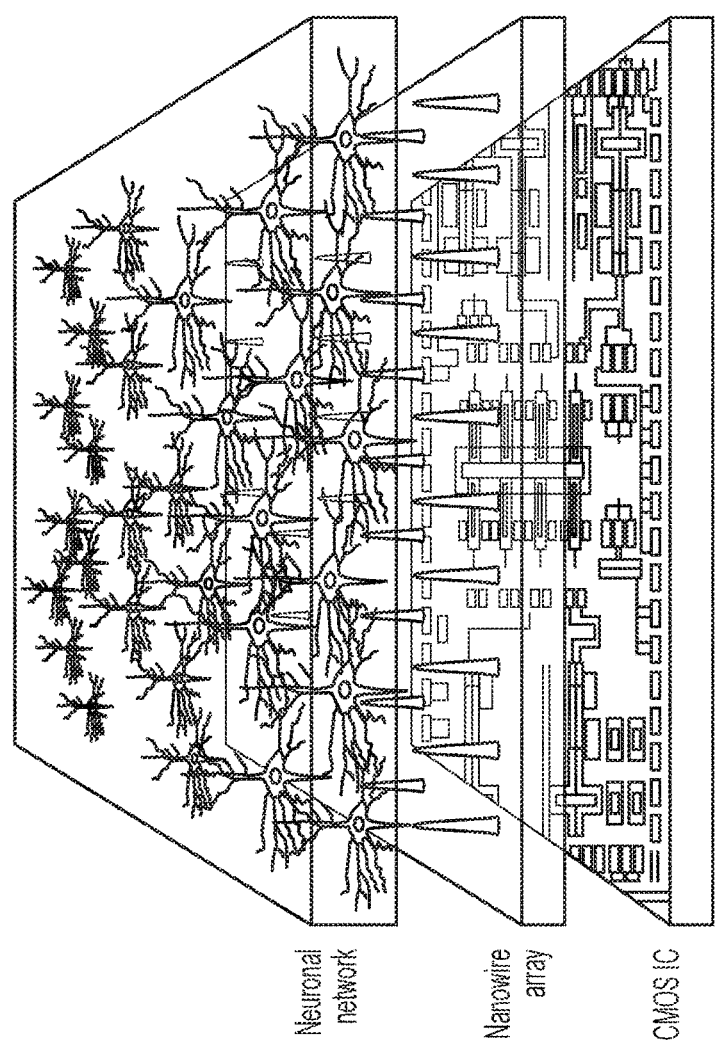
FIG. 15C is a schematic diagram illustrating a representative system for probing a neuronal network comprising a complementary metal-oxide-semiconductor (CMOS) integrated circuit (IC) and a nanowire array, according to some non-limiting embodiments.

The nanowires may be upstanding or substantially oriented vertically, with respect to the surface in some embodiments. For example, on average, the upstanding nanowires may form an angle with respect to a substrate of between about 80° and about 100°, between about 85° and about 95°, or between about 88° and about 92°. In some cases, the average angle is about 90°. Examples of such nanowires may be found in, for example, Int. Pat. Appl. Pub. No. WO 2016/112315, published Jul. 14, 2016, which is incorporated herein by reference in its entirety, and in U.S. Provisional Patent Application Ser. No. 62/580,126, which is incorporated herein by reference in its entirety. As used herein, the term "nanowire" (or "NW") refers to a material in the shape of a wire or rod having a diameter in the range of 1 nm to 1 micrometer (μm). FIG. 15B illustrates a representative nanowire 1530 that is positioned in contact with an metal pad 1506 and a cell 104. The metal pad may be in communication with a corresponding receiver and a stimulator. As further illustrated in FIG. 15C, arrays of nanowires may be used to probe multiple cells. Stimulation and monitoring activity may be performed using CMOS circuits. While FIG. 15C illustrates a nanowire array for probing a neuronal network, nanowires of the types described herein can be used to probe any type of electrogenic cell network.

VI. Conclusion

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, and/or methods described herein, if such features, systems, articles, materials, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An apparatus comprising:
    an electrode configured to electrically contact a sample; and
    a stimulation circuit coupled to the electrode, the stimulation circuit comprising:
        an impedance element having an input terminal and an output terminal coupled to the electrode; and
        a voltage follower coupled between the input terminal and the output terminal of the impedance element, the voltage follower being configured to maintain a substantially constant voltage between the input terminal and the output terminal of the impedance element.

2. The apparatus of claim 1, wherein the impedance element comprises a switched capacitor.

3. The apparatus of claim 2, further comprising a control circuit coupled to the switched capacitor, the control circuit having a frequency tuner.

4. The apparatus of claim 2, wherein the sample and the electrode form a load having a first capacitance, and wherein the switched capacitor has a second capacitance that is lower than the first capacitance.

5. The apparatus of claim 1, wherein the voltage follower comprises one or more transistors arranged in a source follower configuration.

6. The apparatus of claim 5, wherein the one or more transistors comprise a respective gate terminal coupled to the output terminal of the impedance element and a respective source terminal coupled to the input terminal of the impedance element.

7. The apparatus of claim 1, further comprising control circuitry configured to electrically couple a source follower to the input terminal of the impedance element during a first time period and to electrically couple the source follower to the output terminal of the impedance element during a second time period different than the first time period.

8. The apparatus of claim 7, wherein the first time period and the second time period do not overlap in time.

9. The apparatus of claim 1, wherein the electrode comprises a nanowire.

10. The apparatus of claim 9, wherein the electrode comprises an array of nanowires.

11. The apparatus of claim 10, wherein each nanowire of the array of nanowires is individually addressable.

12. The apparatus of claim 1, wherein the sample comprises an electrogenic cell.

13. The apparatus of claim 1, wherein the sample is selected from the group consisting of a brain cell, a heart cell and an endocrine cell.

14. The apparatus of claim 1, further comprising an operational amplifier coupled to the voltage follower; and a receiver circuit coupled to the electrode and comprising a high-frequency cutting filter configured to block ripples generated by the stimulation circuit.

15. The apparatus of claim 1, wherein the stimulation circuit lacks operational amplifiers.

16. The apparatus of claim 1, wherein the stimulation circuit comprises a complementary metal-oxide-semiconductor integrated circuit.

17. The apparatus of claim 1, further comprising a read-out circuit.

18. The apparatus of claim 1, further comprising a receiver.

* * * * *